(12) United States Patent
Nishiyama

(10) Patent No.: US 9,411,932 B2
(45) Date of Patent: Aug. 9, 2016

(54) IMAGE MANAGEMENT APPARATUS

(71) Applicant: OLYMPUS CORPORATION, Tokyo (JP)

(72) Inventor: Takeshi Nishiyama, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/923,691

(22) Filed: Oct. 27, 2015

(65) Prior Publication Data

US 2016/0048637 A1 Feb. 18, 2016

Related U.S. Application Data

(63) Continuation of application No. PCT/JP2014/067569, filed on Jul. 1, 2014.

(30) Foreign Application Priority Data

Aug. 30, 2013 (JP) ................. 2013-180020

(51) Int. Cl.
| | |
|---|---|
| *G06K 9/00* | (2006.01) |
| *G06F 19/00* | (2011.01) |
| *A61B 1/00* | (2006.01) |
| *A61B 1/04* | (2006.01) |
| *G06F 17/30* | (2006.01) |

(52) U.S. Cl.
CPC ............. *G06F 19/321* (2013.01); *A61B 1/00* (2013.01); *A61B 1/0002* (2013.01); *A61B 1/00009* (2013.01); *A61B 1/04* (2013.01);
(Continued)

(58) Field of Classification Search
USPC ........................................................ 382/305
See application file for complete search history.

(56) References Cited

U.S. PATENT DOCUMENTS

2008/0172255 A1* 7/2008 Hirakawa ............. G06F 19/321
  705/3
2008/0232702 A1   9/2008 Kimoto
(Continued)

FOREIGN PATENT DOCUMENTS

| JP | 2007-075163 A | 3/2007 |
| JP | 5242866 B1 | 7/2013 |
| WO | WO 2011/013475 A1 | 2/2011 |

OTHER PUBLICATIONS

International Search Report dated Oct. 7, 2014 issued in PCT/JP2014/067569.

(Continued)

*Primary Examiner* — Yon Couso
(74) *Attorney, Agent, or Firm* — Scully, Scott, Murphy & Presser, PC

(57) ABSTRACT

An image management apparatus includes: a display; a storage unit that stores first operation information, input by a first user, performed on a series of images that are acquired in examination and on the display, such that the first operation information and identification information of the image on which the operation is performed are associated with one another, and stores second operation information, input by a second user, performed on the series of images that are acquired in the examination and on the display, such that the second operation information and identification information of the image on which the operation is performed are associated with one another; and an extraction unit that extracts an image group from the series of images based on whether the identification information of the image associated with the first operation information overlaps with the identification information of the image associated with the second operation information.

14 Claims, 16 Drawing Sheets

(52) U.S. Cl.
CPC ......... *A61B 1/041* (2013.01); *G06F 17/30256* (2013.01); *G06F 17/30274* (2013.01); *G06F 19/3487* (2013.01)

(56) References Cited

U.S. PATENT DOCUMENTS

| | | | |
|---|---|---|---|
| 2009/0051691 | A1 | 2/2009 | Kimoto |
| 2009/0312604 | A1* | 12/2009 | Kimoto .............. A61B 1/00016 600/118 |
| 2011/0249952 | A1 | 10/2011 | Taniguchi |
| 2013/0229503 | A1 | 9/2013 | Taniguchi |
| 2014/0121474 | A1* | 5/2014 | Ciaccio .............. A61B 1/00009 600/301 |

OTHER PUBLICATIONS

Japanese Office Action dated Apr. 7, 2015 issued in JP 2015-503391.
Japanese Office Action dated Jul. 7, 2015 issued in JP 2015-503391.

* cited by examiner

IMAGE MANAGEMENT APPARATUS

CROSS-REFERENCE TO RELATED APPLICATIONS

This application is a continuation of PCT international application Ser. No. PCT/JP2014/067569 filed on Jul. 1, 2014 which designates the United States, incorporated herein by reference, and which claims the benefit of priority from Japanese Patent Application No. 2013-180020, filed on Aug. 30, 2013, incorporated herein by reference.

BACKGROUND

1. Technical Field

The disclosure relates to an image management apparatus for managing an image acquired through an examination using a medical image acquisition device such as a capsule endoscope.

2. Related Art

In recent years, an examination using a capsule endoscope that is introduced into a subject, such as a patient, for capturing an inside of the subject has been known in a field of an endoscope. A capsule endoscope is a device having an imaging function and a wireless communication function mounted in a casing having a shape of a capsule with a size capable of being introduced into the digestive tract of a subject. The capsule endoscope captures the inside of the subject to generate image data, and sequentially transmits the image data wirelessly to an outside of the subject. The image data wirelessly transmitted from the capsule endoscope is temporarily stored in a receiving device provided at the outside of the subject, and then, transferred to an image management apparatus, such as a work station, from the receiving device. Various image processes are performed to the acquired image data in the image management apparatus, whereby a series of images including organs in the subject is generated.

It takes about eight hours for one examination using the capsule endoscope described above, and as much as about 60,000 images are acquired during this examination. Therefore, it takes so much time to observe all of these images. In addition, these images include many images unnecessary for diagnosis, such as images of an outside of the subject or images formed by repeatedly capturing the same site by the capsule endoscope stagnating in the subject. In view of this, a technique of extracting an image useful for diagnosis from a series of images, and presenting the extracted image to a user has conventionally been proposed. For example, Japanese Laid-open Patent Publication No. 2007-75163 discloses a technique of generating a moving image from an image designated through a user's operation and image groups before and after the designated image.

SUMMARY

In some embodiments, an image management apparatus for managing a series of images acquired through an examination includes: a first image storage unit configured to store, for each examination, the series of images and pieces of identification information of the series of images; a display unit configured to display the series of images; an input unit configured to input an operation on an image displayed on the display unit; an operation information storage unit configured to store first operation information indicating the operation, input by a first user, performed on the series of images that are acquired in one examination and displayed on the display unit, such that the first operation information and identification information of the image on which the operation is performed are associated with one another, and to store second operation information indicating the operation, input by a second user different from the first user, performed on the series of images that are acquired in the one examination and displayed on the display unit, such that the second operation information and identification information of the image on which the operation is performed are associated with one another; an image extraction unit configured to determine whether or not the identification information of the image associated with the first operation information overlaps with the identification information of the image associated with the second operation information, and to extract an image group from the series of images based on a result of determination; and a second image storage unit configured to store the image group extracted by the image extraction unit.

The above and other features, advantages and technical and industrial significance of this invention will be better understood by reading the following detailed description of presently preferred embodiments of the invention, when considered in connection with the accompanying drawings.

DETAILED DESCRIPTION

An image management apparatus according to the embodiments of the present invention will be described below with reference to the drawings. The present invention is not limited by these embodiments. The embodiments below describe that a series of images acquired through an examination using a capsule endoscope is managed. However, the image management apparatus according to the present invention can be applied to manage images acquired by various medical image acquisition devices. The same reference signs are used to designate the same elements throughout the drawings.

First Embodiment

Figure 1:
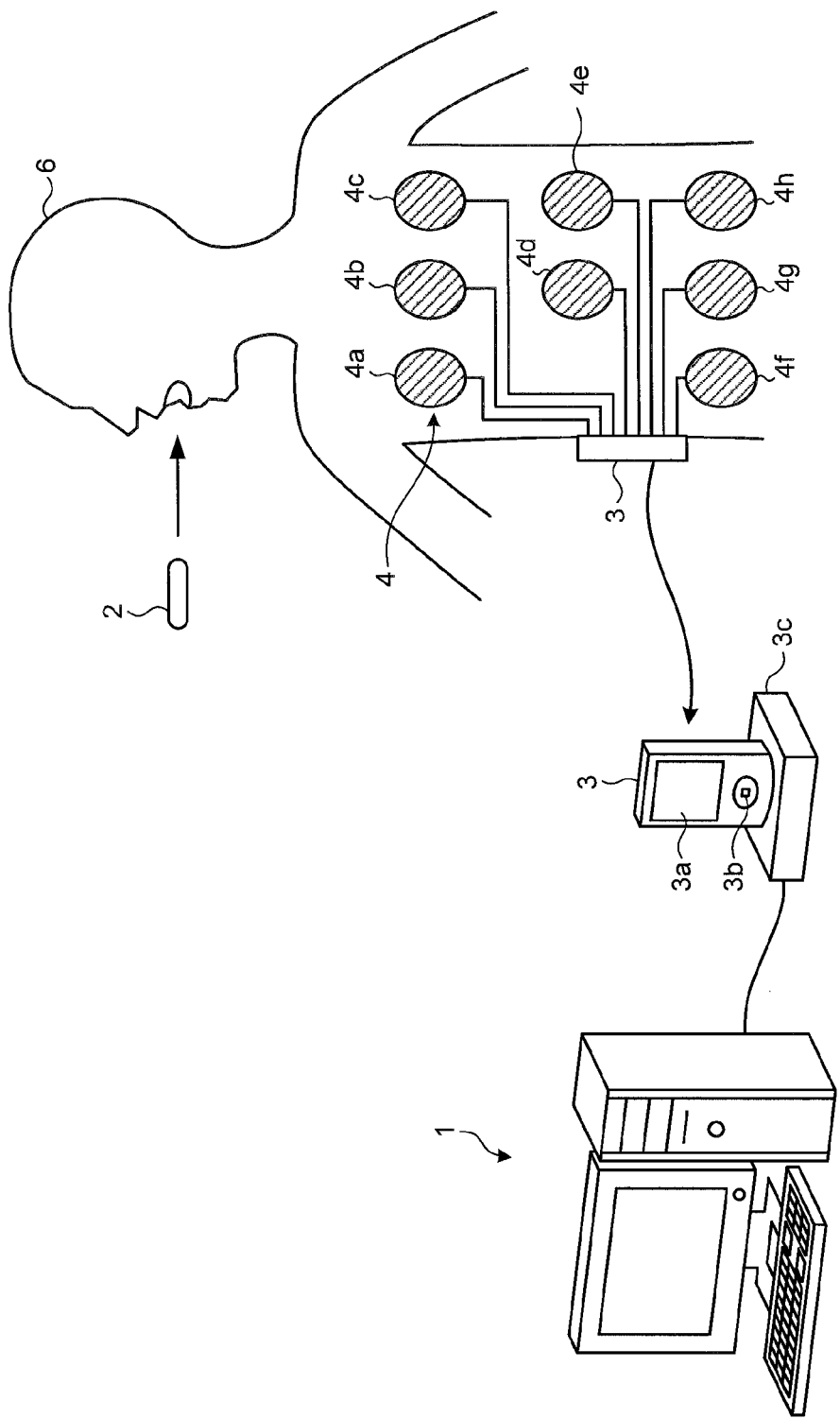
FIG. 1 is a schematic diagram illustrating a capsule endoscope system including an image management apparatus according to a first embodiment of the present invention.

FIG. 1 is a schematic diagram illustrating a capsule endoscope system for an examination using a capsule endoscope. The capsule endoscope system illustrated in FIG. 1 includes an image management apparatus 1 according to a first embodiment of the present invention, a capsule endoscope 2 that is introduced into a subject 6 to capture the inside of the subject 6, generates image data, and wirelessly transmits the generated image data, and a receiving device 3 that receives the image data transmitted from the capsule endoscope 2 via a receiving antenna unit 4 attached to the subject 6.

The image management apparatus 1 is an apparatus managing a series of images acquired through an examination in time series, and constructed from a work station or a general-purpose computer such as a personal computer. The first embodiment describes that images acquired through an examination using the capsule endoscope 2 are managed. However, the image management apparatus 1 can also be applied to manage images acquired by various image acquisition devices other than the capsule endoscope 2. The detailed configuration and operation of the image management apparatus 1 will be described later.

The capsule endoscope 2 is a device including an imaging element such as a CCD, an illumination element such as an LED, a memory, a signal processing unit, a wireless communication unit, and various other components in a capsule casing with a size swallowable by the subject 6. The imaging element is provided at one end of the casing, and captures an image of a predetermined range outside of the casing illuminated by the illumination element, and outputs an imaging signal. The capsule endoscope 2 generates image data by performing a predetermined signal process to the imaging signal outputted from the imaging element, and transmits a wireless signal on which the image data and related information are superimposed.

The receiving device 3 receives the wireless signal transmitted from the capsule endoscope 2 via the receiving antenna unit 4 including a plurality of (eight in FIG. 1) receiving antennas 4a to 4h. Each of the receiving antennas 4a to 4h uses a loop antenna, for example, and is placed on a predetermined position (e.g., a position corresponding to each organ in the subject 6 on a route of the capsule endoscope 2) on the outer surface of the subject 6.

The receiving device 3 demodulates the received wireless signal to acquire the image data and the related information, and stores the image data and the related information into an embedded memory. The receiving device 3 also has a display unit 3a displaying an image based on the acquired image data, and an operation button 3b used for a predetermined operation to the receiving device 3 by a user. The receiving device 3 also includes a data transmission unit having an interface connectable to an USB or a communication network such as wired LAN or wireless LAN, and transfers the image data and related information to an external device via the interface.

Figure 2:
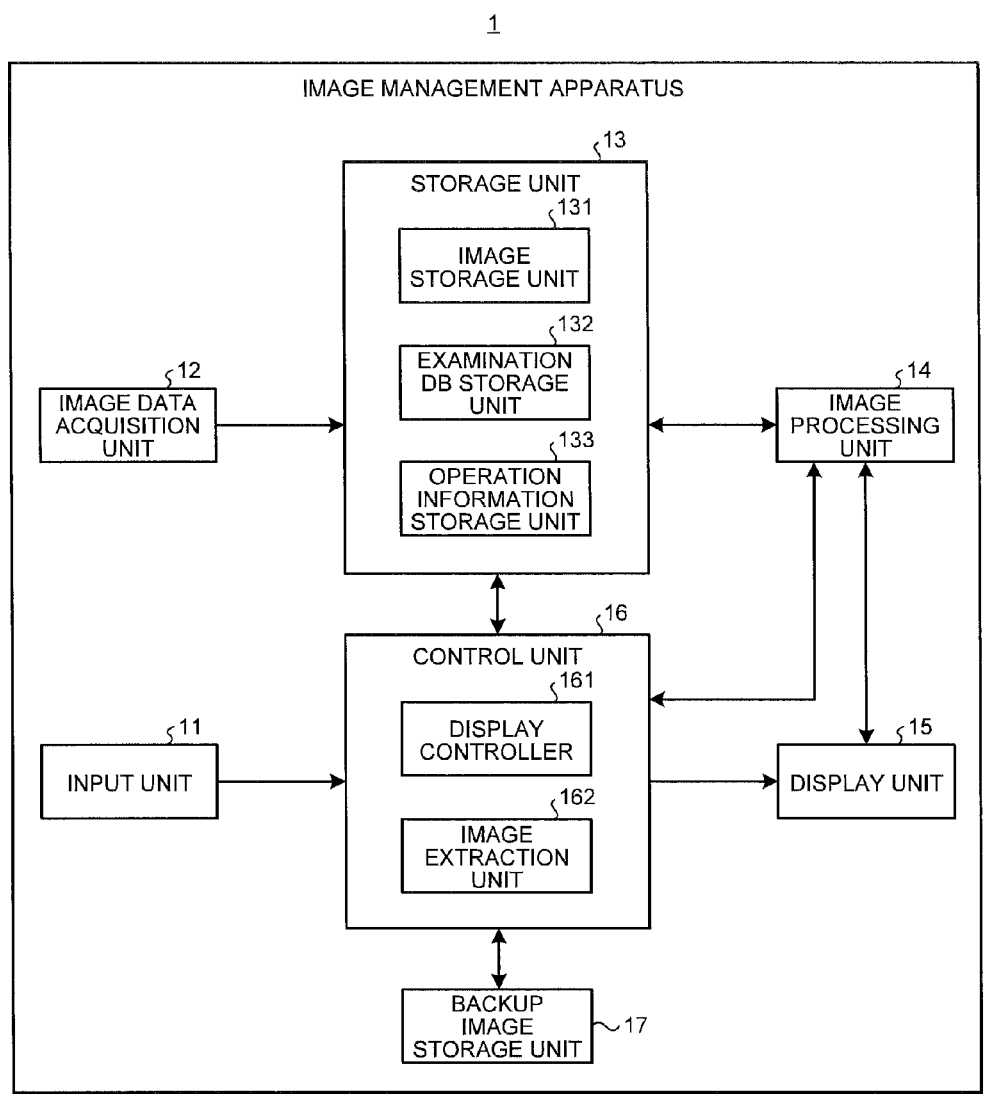
FIG. 2 is a block diagram illustrating a configuration of the image management apparatus according to the first embodiment of the present invention.

FIG. 2 is a block diagram illustrating the configuration of the image management apparatus 1. As illustrated in FIG. 2, the image management apparatus 1 includes an input unit 11, an image data acquisition unit 12, a storage unit 13, an image processing unit 14, a display unit 15, a control unit 16, and a backup image storage unit 17.

The input unit 11 includes an input device such as a keyboard, various buttons, or various switches, and a pointing device such as a mouse or a touch panel, and inputs a signal according to the user's external operation to the control unit 16.

The image data acquisition unit 12 is an interface connectable to an USB or a communication network such as wired LAN or wireless LAN, and includes an USB port or a LAN port. The image data acquisition unit 12 acquires image data and related information through an external device or various networks connected to the USB port, and stores the image data and the related information in the storage unit 13. As illustrated in FIG. 1, the receiving device 3 is set on a cradle 3c connected to the USB port of the image management apparatus 1, whereby the receiving device 3 is connected to the image management apparatus 1 in the first embodiment. With this, image data accumulated in the memory of the receiving device 3 is sequentially retrieved into the image management apparatus 1.

The storage unit 13 is a first storage unit composed of semiconductor memory such as flash memory, RAM, or ROM, a recording medium such as HDD, MO, CD-R, or DVD-R, and a writing and reading device for writing and reading of information to and from the recording medium. The storage unit 13 stores programs and various setting information for allowing the image management apparatus 1 to operate for executing various functions.

The storage unit 13 also includes an image storage unit 131, an examination database (DB) storage unit 132, and an operation information storage unit 133. Among these units, the image storage unit 131 is a first image storage unit storing image data retrieved from the image data acquisition unit 12 or image data on which a predetermined image process is performed by the later-described image processing unit 14.

The examination database storage unit 132 stores an examination database for managing an examination using the capsule endoscope 2. The examination database stores information relating to a patient to be examined, information relating to the detail of the examination, a report having the examination result, link information indicating an address on which the image acquired by the examination is stored, etc.

The operation information storage unit 133 stores information indicating a user's operation to a series of images, which is acquired through the examination and displayed on the display unit 15, for each user in association with identification information of the image on which the operation is performed. For example, an image number corresponding to the order of the images in a series of images is used as the identification information of the image.

The image processing unit 14 is composed of hardware such as CPU. The image processing unit 14 executes a predetermined image process to each of a series of images corresponding to the image data inputted via the image data acquisition unit 12 by reading a program stored in the storage unit 13. Specifically, the image processing unit 14 performs an image process such as a white balance process, demosaicing, color conversion, density conversion (gamma conversion, etc.), smoothing (noise cancellation, etc.), or sharpening (edge enhancement, etc.), to each image. The image processing unit 14 also executes an image process for calculating an average color of each image or an image process for detecting lesion from each image.

The display unit 15 is a display device such as a CRT display or a liquid crystal display, and it displays a screen of a predetermined format including an image or other information under the control of the control unit 16.

The control unit 16 is composed of hardware such as a CPU. The control unit 16 reads the program stored in the storage unit 13 to issue instructions or transfer data to each unit of the image management apparatus 1 based on the signal inputted from the input unit 11. Thus, the control unit 16 generally controls the entire operation of the image management apparatus 1. The control unit 16 also includes a display controller 161 that sequentially displays a series of images of the inside of the subject 6 on the display unit 15 in a predetermined format based on the image data on which the predetermined image process is performed by the image processing unit 14, and an image extraction unit 162 that extracts a plurality of images to be backed up from the series of images and generates a moving image from the extracted images. The moving image described herein may be a moving image of a standard format such as MPEG or AVI, or a moving image of a unique format of the image management apparatus 1.

The backup image storage unit 17 is a second storage unit composed of semiconductor memory such as flash memory, RAM, or ROM, a recording medium such as HDD, MO, CD-R, or DVD-R, and a write/read device performing writing and reading of information to and from the recording medium. The backup image storage unit 17 stores image data for backup of the image data stored in the image storage unit 131. In FIG. 2, the backup image storage unit 17 is mounted in the image management apparatus 1. However, the backup image storage unit 17 may be provided at the outside of the image management apparatus 1. For example, the backup image storage unit 17 may be composed of an external HDD or a server connected through a network.

Figure 3:
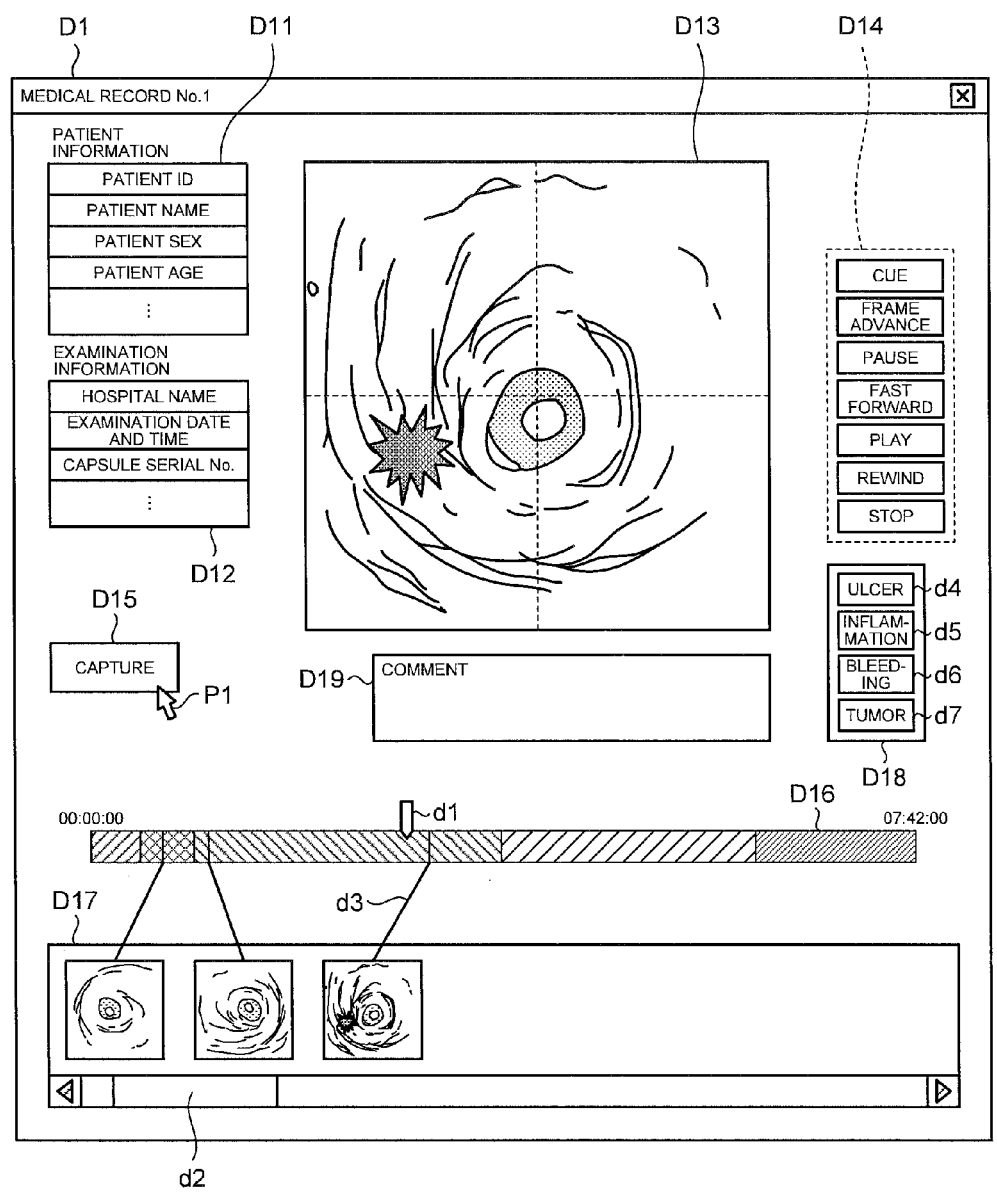
FIG. 3 is a schematic view illustrating an example of a screen displayed when a user such as a doctor observes a series of images.

FIG. 3 is a schematic view illustrating an example of a screen displayed on the display unit 15 under the control of the display controller 161. A screen D1 illustrated in FIG. 3 is a screen displayed when a user such as a doctor observes a series of images. The screen D1 includes a patient information display area D11 in which information relating to a patient who is the subject 6 is displayed, an examination information display area D12 in which information relating to the examination for the subject 6 is displayed, a main display area D13 in which a series of images acquired through the examination is sequentially played back and displayed, a play operation button group D14, a capture button D15, an average color bar D16, a captured image display area D17, a label box D18, and a comment box D19.

The play operation button group D14 is a set of operation buttons used by a user for inputting instructions to control the playback operation of the image in the main display area D13, and includes a cue button, a frame advance button, a pause button, a fast-forward button, a play button, a rewind button, a stop button, etc. When a predetermined pointer operation using the input unit 11 is performed to the playback operation button group D14 (when any one of the operation buttons is clicked by the pointer P1, for example), an operation signal according to this pointer operation is inputted to the display controller 161.

The capture button D15 is a button used by a user to capture an image currently displayed in the main display area D13. When a predetermined pointer operation using the input unit 11 is performed to the capture button D15 (when the capture button D15 is clicked by the pointer P1, for example), a signal for instructing to capture an image currently displayed in the main display area D13 is inputted to the control unit 16 from the input unit 11. With this, a flag by which this image is identified by a captured image is added to this image, and this image is registered as the captured image.

The average color bar D16 is a bar-shaped image in which average colors of a series of images are arranged in time series, and is created based on the average color of each image calculated by the image processing unit 14. A slider d1 indicating the position on the average color bar D16 corresponding to the image currently displayed in the main display area D13 is located on the average color bar D16. The slider d1 moves on the average color bar D16 according to an imaging time of the currently-displayed image during the automatic playback of a series of images in the main display area D13. In the present application, the imaging time means an elapsed time from the imaging start time (examination start time). A user can find when the currently-displayed image is captured by referring to the slider d1. When the user moves the slider d1 along the average color bar D16 by a predetermined pointer operation using the input unit 11 to the slider d1 (by a drag and drop, for example), the image having the imaging time according to the position of the slider d1 can be displayed in the main display area D13.

In the captured image display area D17, compressed images (hereinafter referred to as thumbnail images) of the images registered as captured images are displayed as a list in time series. A slider d2 used for sliding the display range of the thumbnail images is placed in the captured image display area D17. A connection line d3 indicating the correspondence relation between the thumbnail image in the captured image display area D17 and the position on the average color bar D16 may be provided.

A label box D18 includes a plurality of icons d4 to d7 used for adding a label, which is used to classify images according to features observed in the images, to the images. The icons d4 to d7 illustrated in FIG. 3 describe a name of lesion (such as ulcer, inflammation, bleeding, tumor). When any one of the icons d4 to d7 is selected by a predetermined pointer operation using the input unit 11 to the label box D18, a label (name of lesion) associated with the selected icon is added to the image currently displayed in the main display area D13.

The comment box D19 is an area where an input of text information using an input device such as a keyboard is possible, and this box is used when a user inputs a comment to the image currently displayed in the main display area D13. When text information is inputted to the comment box D19, a comment made of the text information is added to the image currently displayed in the main display area D13.

Figure 4:
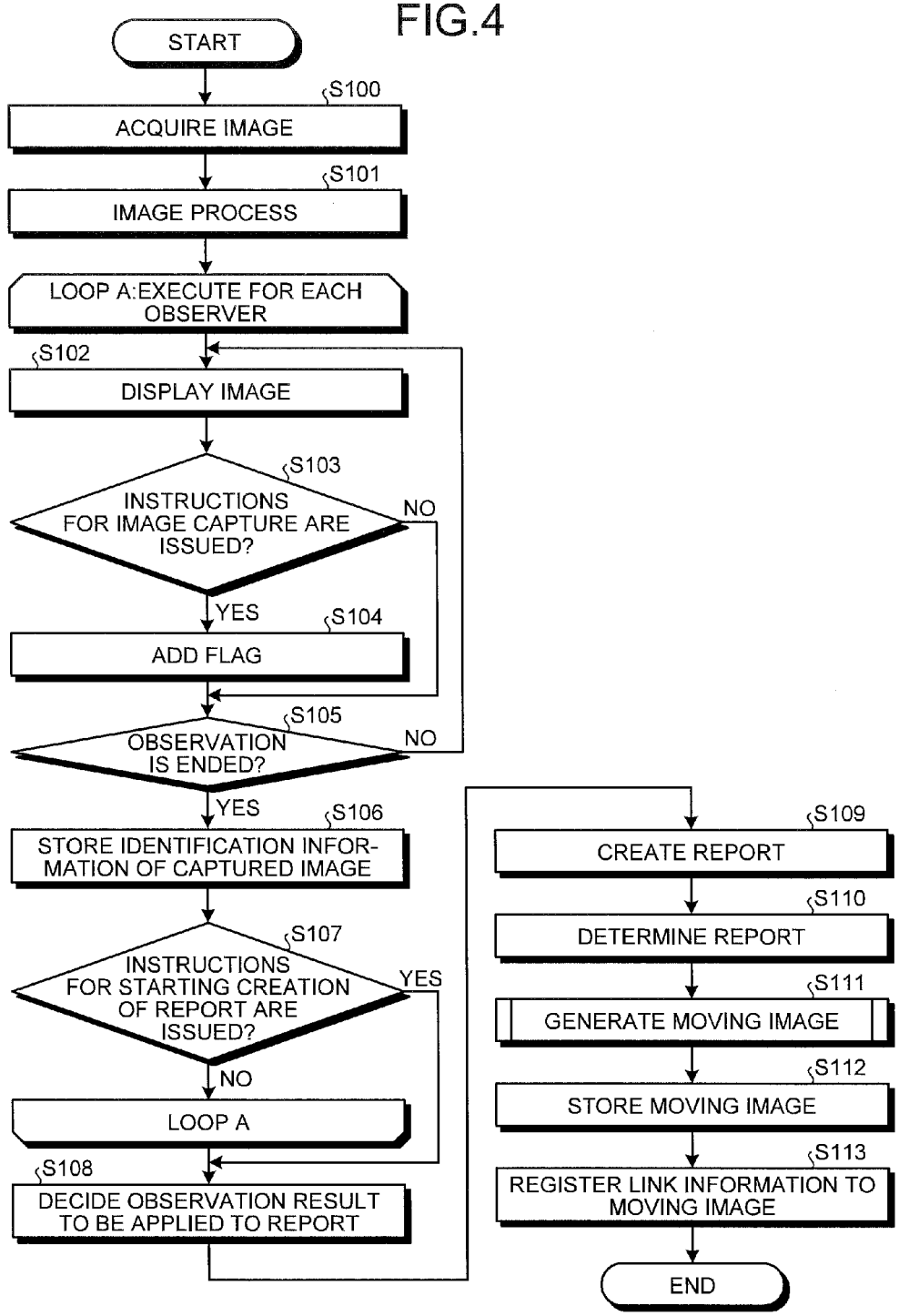
FIG. 4 is a flowchart illustrating an operation of the image management apparatus illustrated in FIG. 2.

Next, the operation of the image management apparatus 1 will be described. FIG. 4 is a flowchart illustrating the operation of the image management apparatus 1.

Firstly, in step S100, the image data acquisition unit 12 acquires image data of a series of images acquired through an examination using the capsule endoscope 2, and stores the image data in the image storage unit 131. In this case, the image data acquisition unit 12 may acquire image data through the cradle 3c from the receiving device 3 illustrated in FIG. 1, or may acquire image data via various communication networks.

In next step S101, the image processing unit 14 performs an image process such as a white balance process, demosaicing, color conversion, density conversion, smoothing, or sharpening, to each of the series of images corresponding to the image data acquired in step S100. The image processing unit 14 also executes an image process for calculating an average color of each image or an image process for detecting lesion from each image. Notably, image data on which the above image process has already been performed may be acquired in step S100. In this case, step S101 is skipped.

Then, the image management apparatus 1 executes a process of a loop A for each user (observer) observing a series of images. Specifically, in step S102, the display controller 161 sequentially displays a series of images based on the image data on which the image process is performed by the image processing unit 14 on the display unit 15 (see FIG. 3).

In next step S103, the control unit 16 determines whether a signal for instructing to capture the image currently displayed in the main display area D13 is inputted or not. When the signal for instructing to capture is inputted (step S103: Yes), the control unit 16 adds a flag by which this image is identified as a captured image to this image (step S104), and displays this image in the captured image display area D17 as compressed. On the other hand, when the signal for instructing to capture the image is not inputted (step S103: No), the operation of the image management apparatus 1 proceeds to step S105.

In step S105, the control unit 16 determines whether it ends the observation of the image by the user or not. For example, when the image currently displayed in the main display area D13 becomes the last image of the series of images, the control unit 16 determines to end the observation. Alternatively, when the user performs a predetermined end operation by using the input unit 11, the control unit 16 may determine to end the observation.

When the control unit 16 does not end the observation (step S105: No), the operation of the image management apparatus 1 proceeds to step S102. On the other hand, when ending the observation (step S105: Yes), the control unit 16 stores the identification information (e.g., image number) of the image (captured image) to which the flag is added in step S104 into the operation information storage unit 133 for each user (step S106).

In next step S107, the control unit 16 determines whether a signal for instructing to start the creation of a report is inputted or not. The signal for instructing to start the creation of the report is inputted according to the operation performed by any one of the users, after all of the plurality of expected users for the series of images finishes the observation. For example, this signal may be inputted by the depression of a specific key or button of the input unit 11, or this signal may be inputted according to a pointer operation using the input unit 11 on the screen of the display unit 15.

Figure 5:
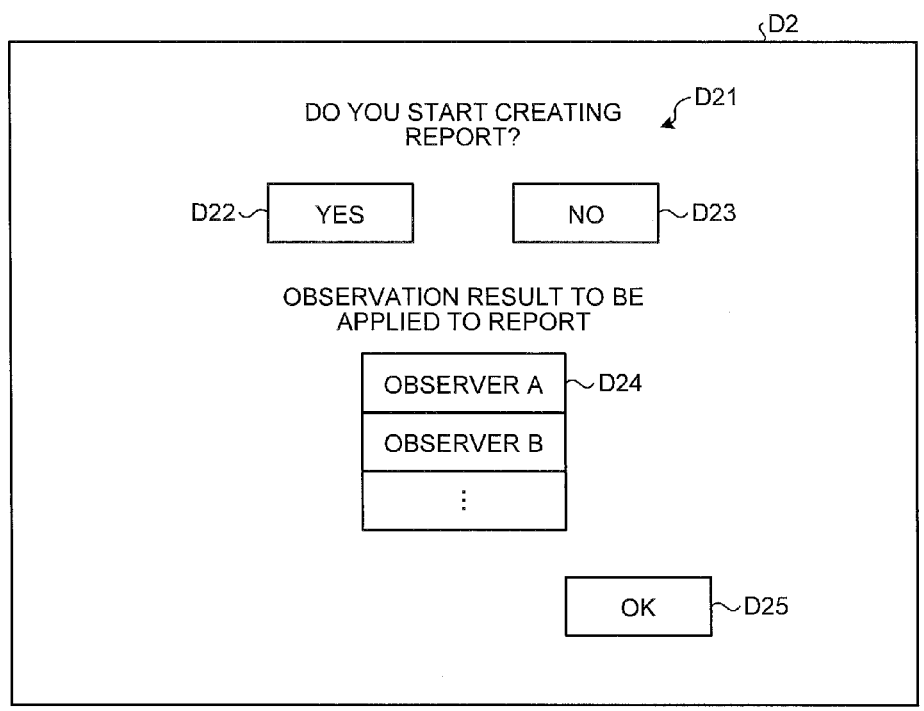
FIG. 5 is a schematic view of an example of a screen displayed when a user finishes observing a series of images.

FIG. 5 is a schematic view of an example of a screen displayed on the display unit 15 when a user finishes observing a series of images. A screen D2 illustrated in FIG. 5 includes a text message D21 asking the user whether he or she starts to create a report or not, icons D22 and D23 used by the user to input whether he or she starts to create a report or not, an observer display box D24 in which the names of the users (e.g., observers "A", "B", . . . ) who have observed the series of images are displayed, and an OK button D25 used for determining the user selected from the names of the users displayed in the observer display box D24. When a predetermined pointer operation using the input unit 11 is performed to the screen D2 (for example, when the icon D22 is clicked), the signal for instructing to start the creation of the report is inputted to the control unit 16.

When the signal for instructing to start the creation of the report is not inputted (step S107: No), the image management apparatus 1 executes the process of the loop A to another user.

On the other hand, when the signal for instructing to start the creation of the report is inputted (step S107: Yes), the control unit 16 decides the observation result, which is to be applied to the report, from the observation results of the plurality of users (step S108). When a user who is in charge of creating a report is determined beforehand from the plurality of users, the control unit 16 decides the observation result by this user as the observation result which is to be applied to the report. Alternatively, the control unit 16 may allow the user to select the observation result which is to be applied to the report, when the signal for instructing to start the creation of the report is inputted. For example, when one of the plurality of users displayed in the observer display box D24 is selected by the pointer operation to the screen D2 using the input unit 11, and the OK button D25 is pressed, a signal selecting this user may be inputted to the control unit 16 from the input unit 11, and with this, the control unit 16 may decide that the observation result by this user is applied to the report.

Figure 6:
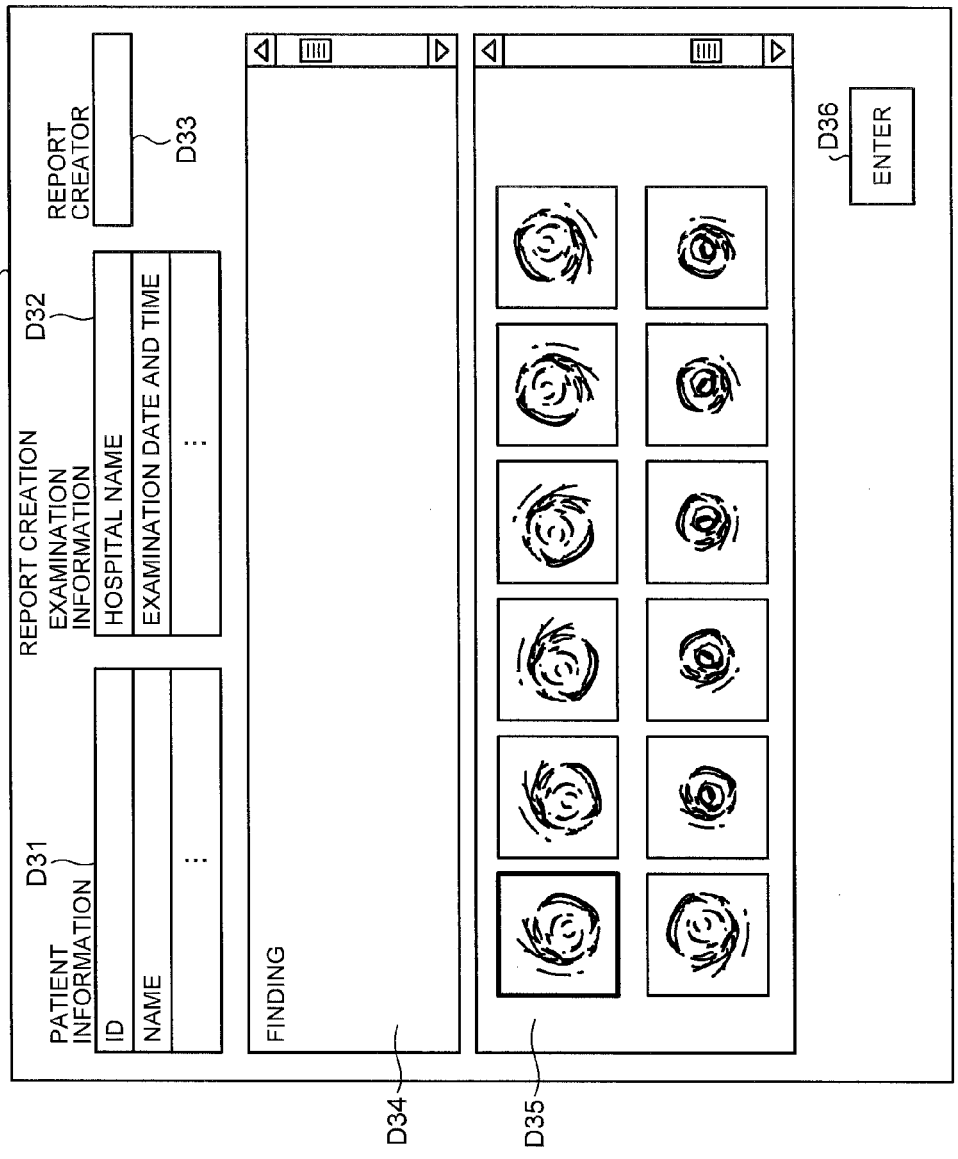
FIG. 6 is a schematic view illustrating an example of a report creation screen.

In step S109, the control unit 16 encourages the user to create a report by displaying an image for the creation of the report on the display unit 15. FIG. 6 is a schematic view illustrating an example of a report creation screen displayed on the display unit 15. The report creation screen D3 includes a patient information display area D31 in which information relating to a patient who is the subject 6 is displayed, an examination information display area D32 in which information relating to an examination performed to the patient is displayed, a report creator display area D33 in which the name of the user in charge of creating a report is displayed, a finding box D34 used by a user to write comments, a captured image display area D35 in which a captured image selected by the user during the observation of the series of images is displayed as compressed, and an enter button D36. The observation result decided in step S108, i.e., the compressed image of the captured image including the observation result which is to be applied to the report, is displayed in the captured image display area D35 among these areas. The user inputs comments in the form of text by the operation on the report creation screen D3 using the input unit 11, selects the image, which is to be attached to the report, from the captured images, and then, presses the enter button D36.

In step S110, the control unit 16 determines the content of the report inputted in the form of text by the user, and stores the resultant into the storage unit 13.

Figure 7:
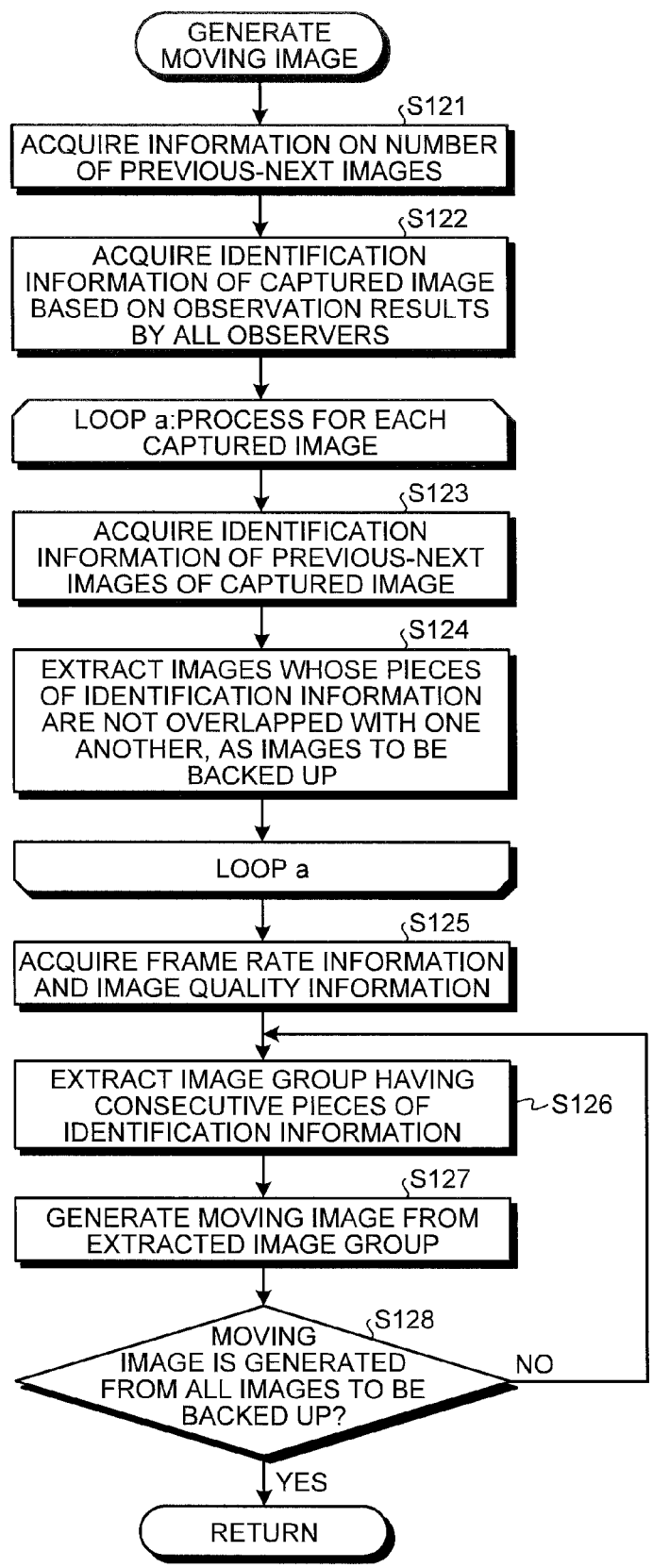
FIG. 7 is a flowchart illustrating a process of generating a moving image according to the first embodiment of the present invention.
Figure 8:
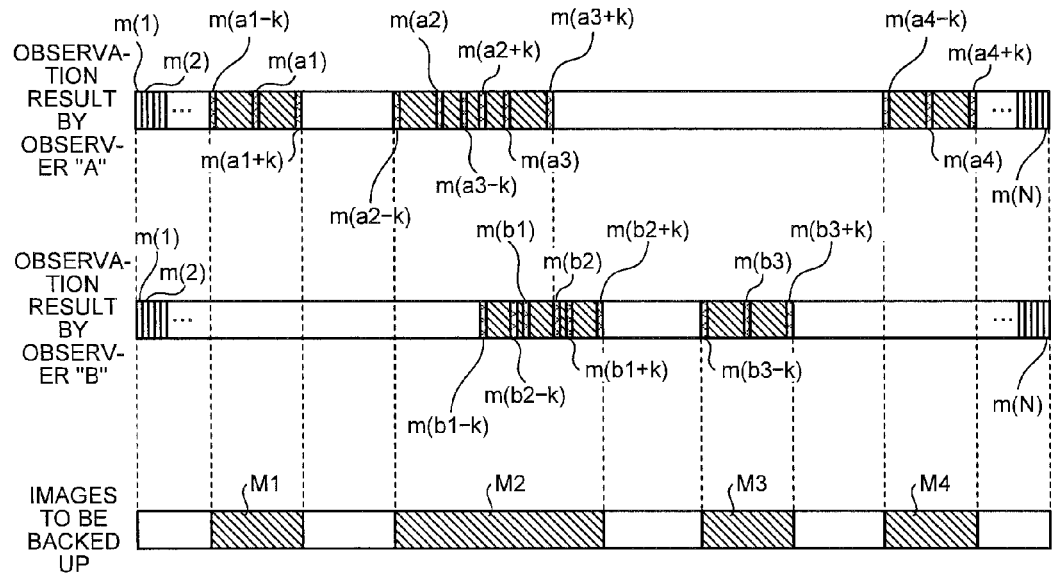
FIG. 8 is a schematic diagram illustrating the process of generating a moving image according to the first embodiment of the present invention.

In next step S111, the control unit 16 generates a moving image which is to be stored as a backup of the series of images. In the present first embodiment, the captured image and a predetermined number of images before and after the captured image are extracted, and a moving image is generated from more than one extracted consecutive images. The generated moving image is stored as a backup. FIG. 7 is a flowchart illustrating a process of generating a moving image. FIG. 8 is a schematic diagram illustrating the process of generating a moving image.

Firstly, in step S121, the image extraction unit 162 acquires information on the number of images (hereinafter referred to as previous images and next images, and they are collectively referred to as previous-next image) extracted before and after the captured image from the storage unit 13. The number of the previous images and the number of the next images may be the same or different from each other. In the present first embodiment, the number of the previous images and the number of the next images are each set as k (k is a natural number).

In next step S122, the image extraction unit 162 acquires the identification information of the captured image from the operation information storage unit 133 based on the observation results by all users (observers) who have observed the series of images. In the present first embodiment, an image number is used as identification information. For example, as illustrated in FIG. 8, when two users who are an observer "A" and an observer "B" observe a series of images m(1) to m(N) (N is a natural number), the image extraction unit 162 acquires image numbers a1, a2, a3, and a4 of the images m(a1), m(a2), m(a3), and m(a4) captured by the observer "A" and image numbers b1, b2, and b3 of the images m(b1), m(b2), and m(b3) captured by the observer "B". In this case, 1≤a1<a2<a3<a4≤N, and 1≤b1<b2<b3≤N.

Then, the image extraction unit 162 executes the process of a loop a for each captured image whose identification information is acquired. Specifically, in step S123, the image extraction unit 162 sequentially acquires the identification information of each of the previous-next images of the captured image.

In next step S124, the image extraction unit 162 determines whether or not the identification information of the captured image to be processed and the pieces of identification information of the previous-next images are overlapped with the pieces of identification information of the images which have already been extracted to be backed up. The image extraction unit 162 newly extracts images whose pieces of identification information are not overlapped with one another, as images to be backed up.

According to the process of the loop a, the images described below are extracted in the case of FIG. 8, for example. Firstly, a captured image m(a1), its previous images m(a1−k) to m(a1−1), and its next images m(a1+1) to m(a1+k) are extracted as images to be backed up. In FIG. 8, the images extracted to be backed up are hatched or shaded in a lattice.

Next, a captured image m(a2), its previous images m(a2−k) to m(a2−1), and its next images m(a2+1) to m(a2+k) are extracted to be backed up, since the image numbers thereof are not overlapped with the image numbers of the images m(a1−k) to m(a1+k) that have already been extracted.

As for a captured image m(a3), its previous images m(a3−k) to m(a3−1), and its next images m(a3+1) to m(a3+k), some of the image numbers of the previous images m(a3−k) to m(a3−1) are overlapped with some of the image numbers of the next images m(a2+1) to m(a2+k) of the image m(a2). Therefore, only the images m(a2+k+1) to m(a3+k) whose image numbers are not overlapped are extracted as images to be backed up.

As for a captured image m(b1), its previous images m(b1−k) to m(b1−1), and its next images m(b1+1) to m(b1+k), some of the image numbers of these images are overlapped with some of the image numbers of the images m(a2+1) to m(a3+k) which have already been extracted. Therefore, only the images m(a3+k+1) to m(b1+k) whose image numbers are not overlapped are extracted as images to be backed up.

Similarly, the captured images m(b2), m(b3), and m(a4) are sequentially processed, whereby images m(b1+k+1) to m(b2+k), m(b3−k) to m(b3+k), and m(a4−k) to m(a4+k) are extracted as images to be backed up.

After the process of the loop a is executed to all captured images, the image extraction unit 162 acquires frame rate information and image quality information of a moving image in step S125.

In next step S126, the image extraction unit 162 extracts, from the images extracted by the process of the loop a, an image group in which pieces of identification information are consecutive. For example, in the case of FIG. 8, the images m(a1−k) to m(a1+k), m(a2−k) to m(b2+k), m(b3−k) to m(b3+k), and m(a4−k) to m(a4+k), which have consecutive image numbers, are each extracted as one image group. Specifically, when there are overlapped images among the image groups each including the captured image and its previous-next images, these image groups are combined as one group.

In next step S127, the image extraction unit 162 generates a moving image from each image group extracted in step S126 by applying the frame rate information and image quality information acquired in step S125. With this, four moving images M1 to M4 are generated in FIG. 8.

In step S128, the image extraction unit 162 determines whether or not a moving image is generated from all images to be backed up which are extracted by the process of the loop a. When a moving image is generated from all images to be backed up (step S128: Yes), the process returns to the main routine. On the other hand, images to be backed up from which a moving image is not yet generated are left (step S128: No), the process returns to step S126.

Referring again to FIG. 4, the control unit 16 stores the moving image generated in step S111 into the backup image storage unit 17 in step S112 next to step S111.

In step S113, the control unit 16 also registers link information to the moving image stored in step S112 to the database relating to the examination stored in the examination database storage unit 132.

Thereafter, the operation of the image management apparatus 1 for the series of images is ended.

As described above, according to the first embodiment, a moving image is generated from images extracted based on the images captured by a plurality of users in a series of images acquired through an examination using a capsule endoscope, and this moving image is stored as a backup. Accordingly, images useful for diagnosis can be extracted without any omission, and backups can be created with less storage capacity than in the background art.

First Modification

Figure 9:
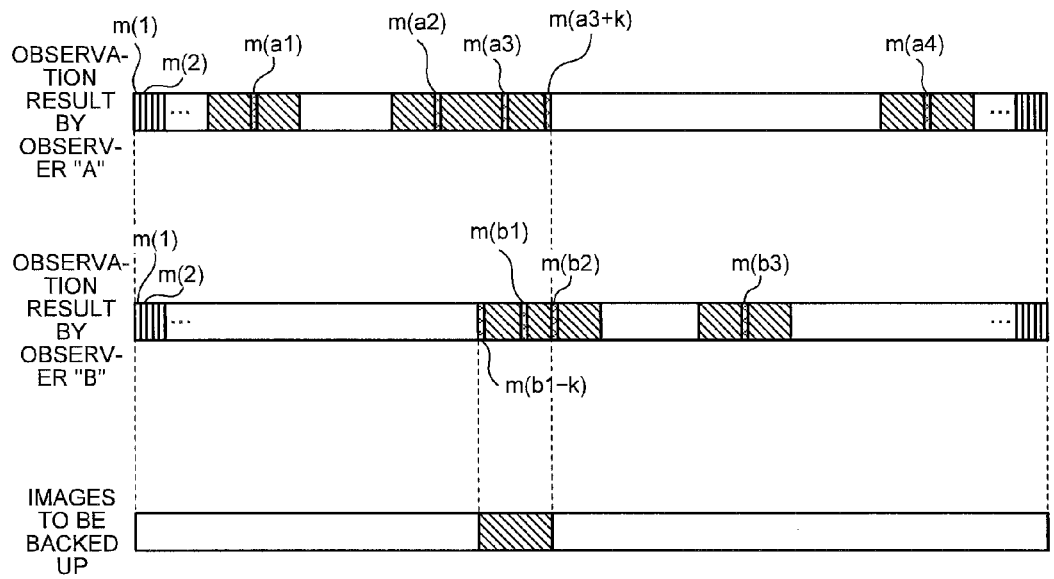
FIG. 9 is a schematic diagram illustrating a process of generating a moving image according to a first modification of the first embodiment of the present invention.

Next, a first modification of the first embodiment of the present invention will be described. FIG. 9 is a schematic diagram illustrating a process of generating a moving image according to the first modification.

In the above first embodiment, the captured image by at least one user and its previous-next images are extracted as images to be backed up. However, only images common to all users in the captured images by all users and their previous-next images may be extracted as images to be backed up. For example, as illustrated in FIG. 9, images m(b1−k) to m(a3+k) whose pieces of identification information (image numbers) are overlapped with one another may be extracted from images m(a1), m(a2), m(a3), and m(a4) captured by an observer "A" and their previous-next images, and images m(b1), m(b2), and m(b3) captured by an observer "B" and their previous-next images. Based on these images, a moving image may be generated and stored as a backup.

According to the present first modification, images considered to be useful for diagnosis by a plurality of users can be backed up.

Second Embodiment

Next, a second embodiment of the present invention will be described.

In the above first embodiment, each user observes an image displayed in the display unit 15 after the examination based on the image transferred to the image management apparatus 1, and a moving image as a backup is created based on this observation result. However, a user may observe an image in real time during the examination, and a moving image as a backup may be created based on an image captured during the observation.

Figure 10:
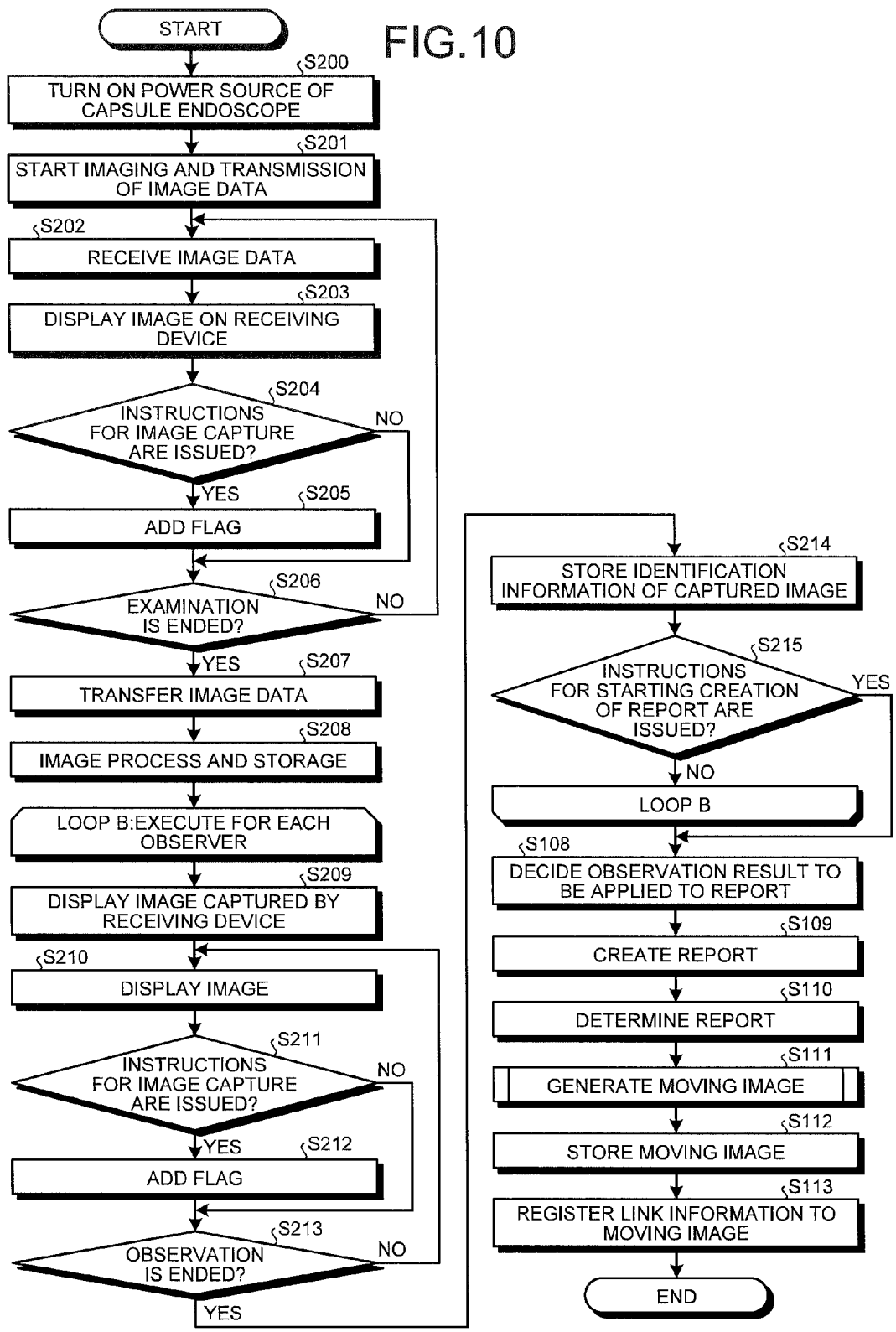
FIG. 10 is a flowchart illustrating an operation of a capsule endoscope system according to a second embodiment of the present invention.

FIG. 10 is a flowchart illustrating an operation of a capsule endoscope system according to the second embodiment. Notably, the configuration of the capsule endoscope system according to the present second embodiment is similar to that in the first embodiment (see FIG. 2).

When a power source of the capsule endoscope 2 is turned on in step S200, the capsule endoscope 2 starts imaging and wireless transmission of image data (step S201). With this, the receiving device 3 receives image data (step S202).

In step S203, the receiving device 3 performs a predetermined signal process to the received image data, and displays the resultant image on a display unit 3a. After confirming that the image captured by the capsule endoscope 2 is displayed on the display unit 3a, a user such as a doctor allows a patient who is the subject 6 to swallow the capsule endoscope 2.

In step S204, the receiving device 3 determines whether an operation for instructing to capture the image currently displayed on the display unit 3a is performed or not. The operation instructing to capture includes a predetermined operation of pressing an operation button 3b while an image is displayed, for example. When the operation instructing to capture the image is performed (step S204: Yes), the receiving device 3 adds a flag for extracting the currently-displayed image as a captured image to the image data (step S205). On the other hand, when the operation instructing to capture the image is not performed (step S204: No), the operation of the receiving device 3 proceeds to step S206.

If the user such as a doctor does not need to capture an image in real time after confirming that the capsule endoscope 2 normally captures an image of an inside of the subject 6, he or she may set the subject 6 free from an examination room, and allow the subject 6 to be free till a predetermined time with the receiving device 3.

In step S206, the receiving device 3 determines whether the examination is finished or not. For example, the receiving device 3 determines that the examination is finished when the transmission of image data from the capsule endoscope 2 is stopped or an operation instructing to stop the examination is performed for the receiving device 3.

When the examination is not yet finished (step S206: No), the operation of the receiving device 3 proceeds to step S202. On the other hand, when the examination is finished (step S206: Yes), the receiving device 3 transfers image data to the image management apparatus 1 (step S207). The transfer of the image data is started when the user sets the receiving device 3 on the cradle 3c connected to the image management apparatus 1.

In step S208, the image management apparatus 1 performs a predetermined image process on the image data received from the receiving device 3, and stores the image data on which the image process has been performed, into the storage unit 13.

Then, the image management apparatus 1 executes a process of a loop B for each user (observer) observing a series of images. Specifically, in step S209, the display controller 161 firstly extracts the image (captured image) having the flag added thereto in step S205, and displays the extracted image in the captured image display area D17 (see FIG. 3) of the display unit 15. In this case, the user may delete the images which are not necessarily captured from the captured image display area D17 by referring to the captured image display area D17. The images can be deleted by a predetermined pointer operation to the screen D1 using the input unit 11 (for example, by double-clicking the desired image displayed in the captured image display area D17). When a user other than the user performing the examination (e.g., the user performing an image capture with the receiving device 3) observes the series of images with the image management apparatus 1, the image captured with the receiving device 3 may not be displayed in the captured image display area D17.

In next step S210, the display controller 161 sequentially displays a series of images based on the image data stored in the storage unit 13 on the main display area D13 of the display unit 15.

In step S211, the control unit 16 determines whether a signal for instructing to capture the image currently displayed in the main display area D13 is inputted or not. This determination method is similar to that in the first embodiment (see step S103 in FIG. 4).

When the signal for instructing to capture an image is inputted (step S211: Yes), the control unit 16 adds a flag by which this image is identified as a captured image to this image (step S212), and displays this image in the captured image display area D17 as compressed. On the other hand, when the signal for instructing to capture an image is not inputted (step S211: No), the operation of the image management apparatus 1 proceeds to step S213.

In step S213, the control unit 16 determines whether the observation of the image by the user is ended or not. This determination method is similar to that in the first embodiment (see step S105 in FIG. 4).

When the control unit 16 does not end the observation (step S213: No), the operation of the image management apparatus 1 returns to step S210. On the other hand, when ending the observation (step S213: Yes), the control unit 16 stores the identification information (e.g., image number) of the image (captured image) to which the flag is added in step S205 and step S212 into the operation information storage unit 133 for each user (step S214).

In next step S215, the control unit 16 determines whether a signal for instructing to start the creation of a report is inputted or not. This determination method is similar to that in the first embodiment (see step S107 in FIG. 4).

When the signal for instructing to start the creation of the report is not inputted (step S215: No), the image management apparatus 1 executes the process of the loop B to another user.

On the other hand, when the signal for instructing to start the creation of the report is inputted (step S215: Yes), the operation of the image management apparatus 1 proceeds to step S108. The operations in the following steps S108 to S113 are similar to those in the first embodiment.

As described above, according to the second embodiment, a moving image can be generated as a backup based on the images captured by a user such as a doctor out of the images displayed in real time in the receiving device 3 during the examination. Accordingly, backups of images, which are recognized by a user such as a doctor that confirmation is needed during an examination, can be created without any omission.

Third Embodiment

Next, a third embodiment of the present invention will be described.

In the above first embodiment, a moving image for a backup is generated based on all images captured by users. However, a moving image for a backup may be crated based on an image to which a label, comment, or annotation is attached, i.e., an image specially interested by a user, out of the captured images.

A label, comment, and annotation can be added by a predetermined operation on the screen D1 (see FIG. 3) using the input unit 11. For example, a label can be added by selecting any one of the icons d4 to d7 provided in the label box D18.

A comment can be added by inputting a text in the comment box D19. An annotation can be added as described below. Specifically, a screen for adding an annotation is displayed by a predetermined pointer operation (for example, a right click) to a captured image displayed in the captured image display area D17, and a graphic (arrow, ellipse, rectangle, triangle, etc.) or a text is inputted on the image in this screen (not illustrated in the figure).

In the present third embodiment, the control unit 16 acquires the identification information of the image to which a label, comment, or annotation is added, out of the captured images in step S122 in FIG. 7. In the following steps S123 to S128, the process is performed based on the identification information acquired in step S122 to generate a moving image.

According to the third embodiment described above, a moving image as a backup is generated based on an image especially interested by each user out of captured images, whereby storage capacity needed for backups can further be reduced.

Fourth Embodiment

Next, a fourth embodiment of the present invention will be described.

In the above first embodiment, a moving image for a backup is generated based on the image captured by each user during the observation of a series of images. However, upon creating a report, a user in charge of creating a report sometimes selects an image other than the image captured by oneself for the report. In such case, a moving image as a backup may be generated based on the image selected for the report.

Figure 11:
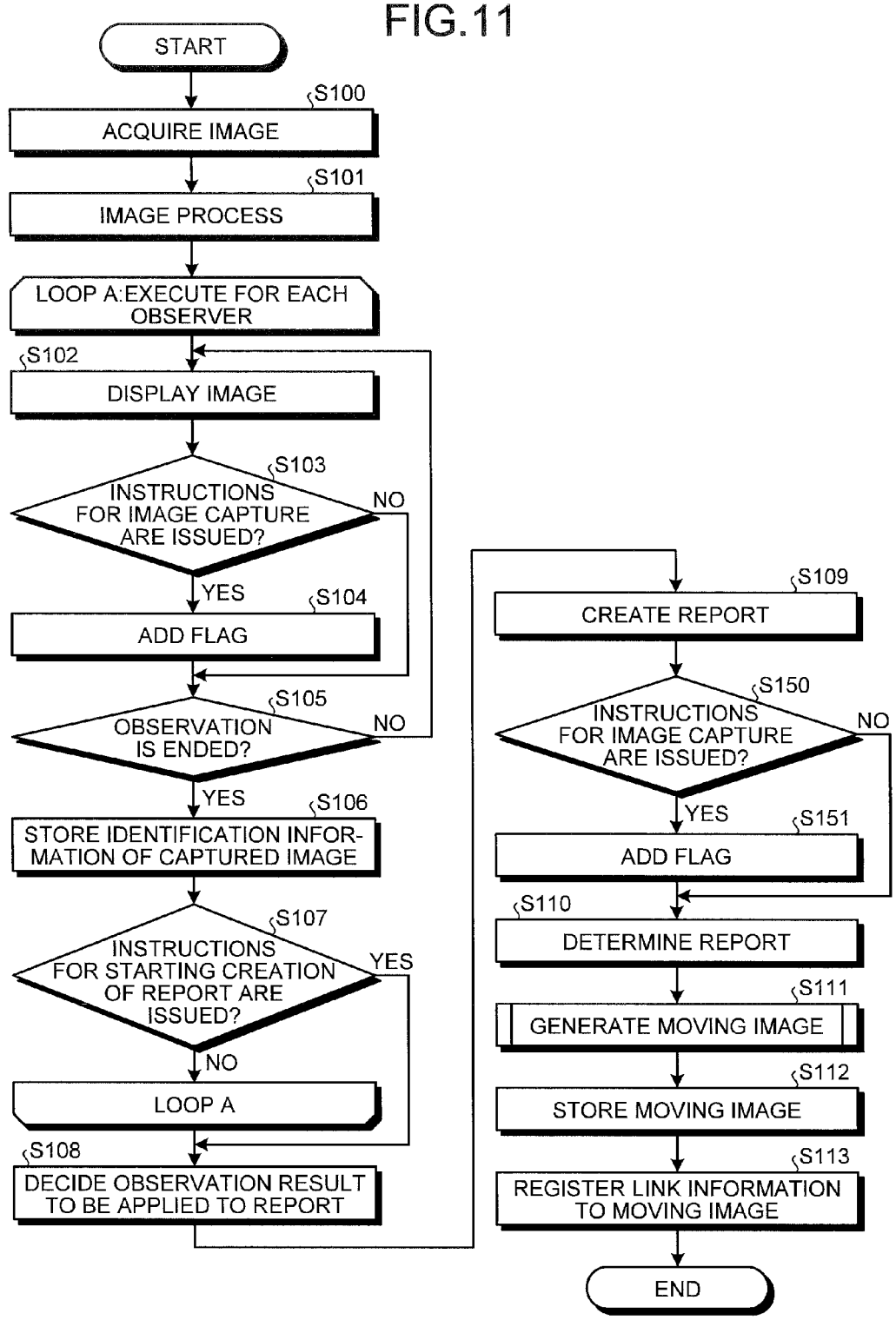
FIG. 11 is a flowchart illustrating an operation of an image management apparatus according to a fourth embodiment of the present invention.
Figure 12:
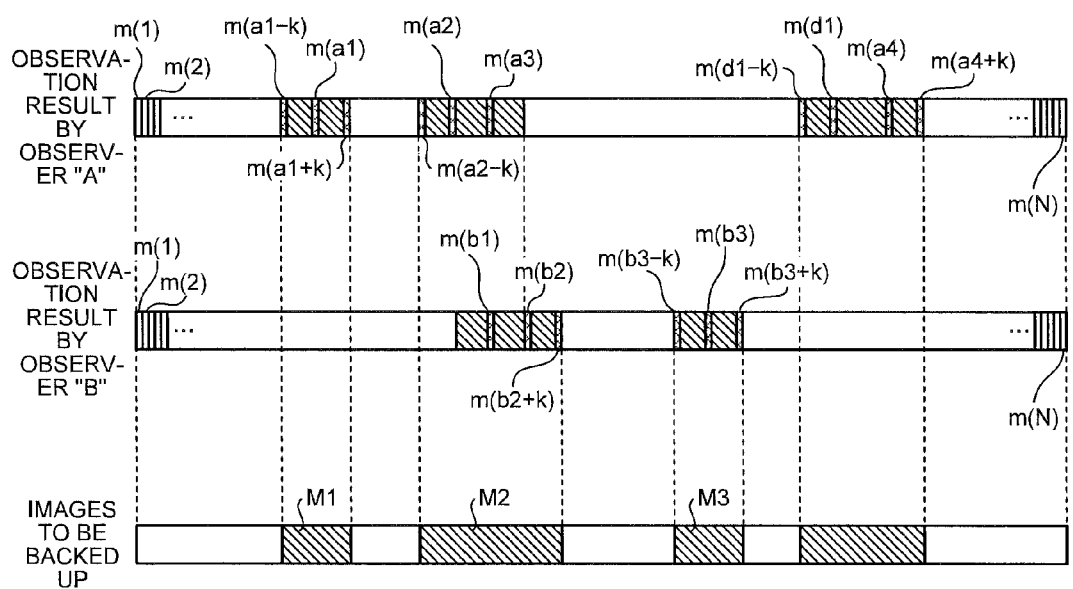
FIG. 12 is a schematic diagram illustrating a process of generating a moving image according to the fourth embodiment of the present invention.

FIG. 11 is a flowchart illustrating an operation of an image management apparatus according to the fourth embodiment of the present invention. FIG. 12 is a schematic diagram illustrating a process of generating a moving image according to the fourth embodiment of the present invention. Steps S100 to S109 in FIG. 11 are similar to those in the first embodiment (see FIG. 4).

In step S150 subsequent to step S109, the control unit 16 determines whether a signal for instructing to capture an image other than the image already captured is inputted or not. When the signal for instructing to capture is inputted (step S150: Yes), the control unit 16 adds a flag by which this image is identified as a captured image to this image (step S151). On the other hand, when the signal for instructing to capture an image is not inputted (step S150: No), the operation of the image management apparatus 1 proceeds to step S110.

The operations in steps S110 to S113 are similar to those in the first embodiment. However, in step S111, a moving image is generated based on the identification information of the image to which a flag is added in steps S104 and S151. Specifically, in step S122 in FIG. 7, the identification information of the image m(d1) captured by the observer "A" for creating a report is extracted in addition to the pieces of identification information of the images m(a1), m(a2), m(a3), m(b1), m(b2), m(b3), and m(a4) captured by the observers "A" and "B". Here, 1≤d1≤N. Then, in next steps S123 to S128, the process is performed based on these pieces of identification information. As a result, the images m(a1−k) to m(a1+k), m(a2−k) to m(b2+k), m(b3−k) to m(b3+k), and m(d1−k) to m(a4+k) are extracted as images to be backed up, and moving images, each including each image group, are generated.

According to the present fourth embodiment, a moving image as a backup is generated based on the image selected for creating a report in addition to the observation result by a plurality of users to a series of images. Therefore, backups for images useful for diagnosis can be created without any omission.

Fifth Embodiment

Next, a fifth embodiment of the present invention will be described.

Figure 13:
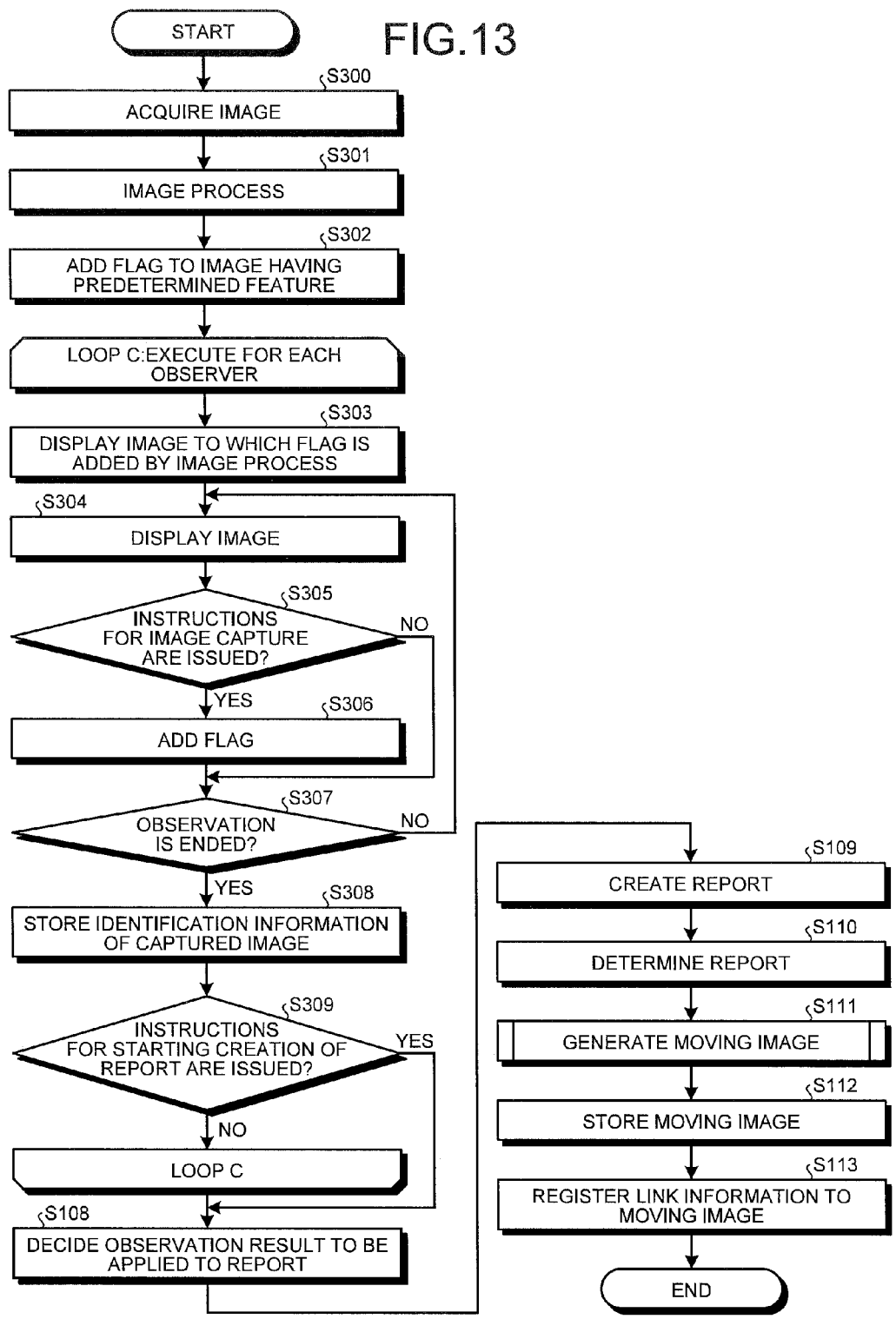
FIG. 13 is a flowchart illustrating an operation of an image management apparatus according to a fifth embodiment of the present invention.

FIG. 13 is a flowchart illustrating an operation of an image management apparatus according to the fifth embodiment of the present invention. Notably, the configuration of the image management apparatus according to the fifth embodiment is similar to that in the first embodiment (see FIG. 2). The present fifth embodiment is characterized in that a moving image as a backup is generated based on an image determined to be noteworthy by an image process, in addition to an image captured by each user.

Firstly, in step S300, the image data acquisition unit 12 acquires image data of a series of images acquired through an examination using the capsule endoscope 2, and stores the image data in the image storage unit 131.

In next step S301, the image processing unit 14 performs an image process such as a white balance process, demosaicing, color conversion, density conversion (gamma conversion, etc.), smoothing (noise cancellation, etc.), or sharpening (edge enhancement, etc.), to the image data acquired in step S300. The image processing unit 14 also executes an image process for detecting an average color of each image or an image process for detecting lesion, such as ulcer, bleeding, or tumor, from each image.

In next step S302, the image processing unit 14 adds a flag to an image having a predetermined feature based on the result of the image process, the flag indicating that the image has the predetermined feature. Specific examples of the image having a predetermined feature include an image in which a specific feature data is equal to or higher than a reference value, an image from which a specific lesion is detected, or an image in which a degree of a detected lesion is equal to or higher than a predetermined reference.

Then, the image management apparatus 1 executes a process of a loop C for each user (observer) observing a series of images. Specifically, in step S303, the display controller 161 firstly extracts the image having the flag added thereto in step S302, and displays the extracted image in the captured image display area D17 (see FIG. 3) of the display unit 15. In this case, the user may delete the images which are not necessarily kept captured from the captured image display area D17 by referring to the captured image display area D17. The images can be deleted by a predetermined pointer operation to the screen D1 using the input unit 11 (for example, by double-clicking the image displayed in the captured image display area D17). A flag indicating that the user deletes this image is further added to the image deleted from the captured image display area D17.

In next step S304, the display controller 161 sequentially displays a series of images based on the image data stored in the storage unit 13 on the main display area D13 of the display unit 15.

In step S305, the control unit 16 determines whether a signal for instructing to capture the image currently displayed in the main display area D13 is inputted or not. This determination method is similar to that in the first embodiment (see step S103 in FIG. 4).

When the signal for instructing to capture an image is inputted (step S305: Yes), the control unit 16 adds a flag by which this image is identified as a captured image to this image (step S306), and displays this image in the captured image display area D17 as compressed. On the other hand, when the signal for instructing to capture an image is not inputted (step S305: No), the operation of the image management apparatus 1 proceeds to step S307.

In step S307, the control unit 16 determines whether the observation of the image by the user is ended or not. This determination method is similar to that in the first embodiment (see step S105 in FIG. 4).

When the control unit 16 does not end the observation (step S307: No), the operation of the image management apparatus 1 proceeds to step S304. On the other hand, when ending the observation (step S307: Yes), the control unit 16 stores the identification information (e.g., image number) of the image (captured image) to which the flag is added in step S302 and step S306 into the operation information storage unit 133 for each user (step S308).

In next step S309, the control unit 16 determines whether a signal for instructing to start the creation of a report is inputted or not. This determination method is similar to that in the first embodiment (see step S107 in FIG. 4).

When the signal for instructing to start the creation of the report is not inputted (step S309: No), the image management apparatus 1 executes the process of the loop C to another user.

On the other hand, when the signal for instructing to start the creation of the report is inputted (step S309: Yes), the operation of the image management apparatus 1 proceeds to step S108. The operations in the following steps S108 to S113 are similar to those in the first embodiment.

Figure 14:
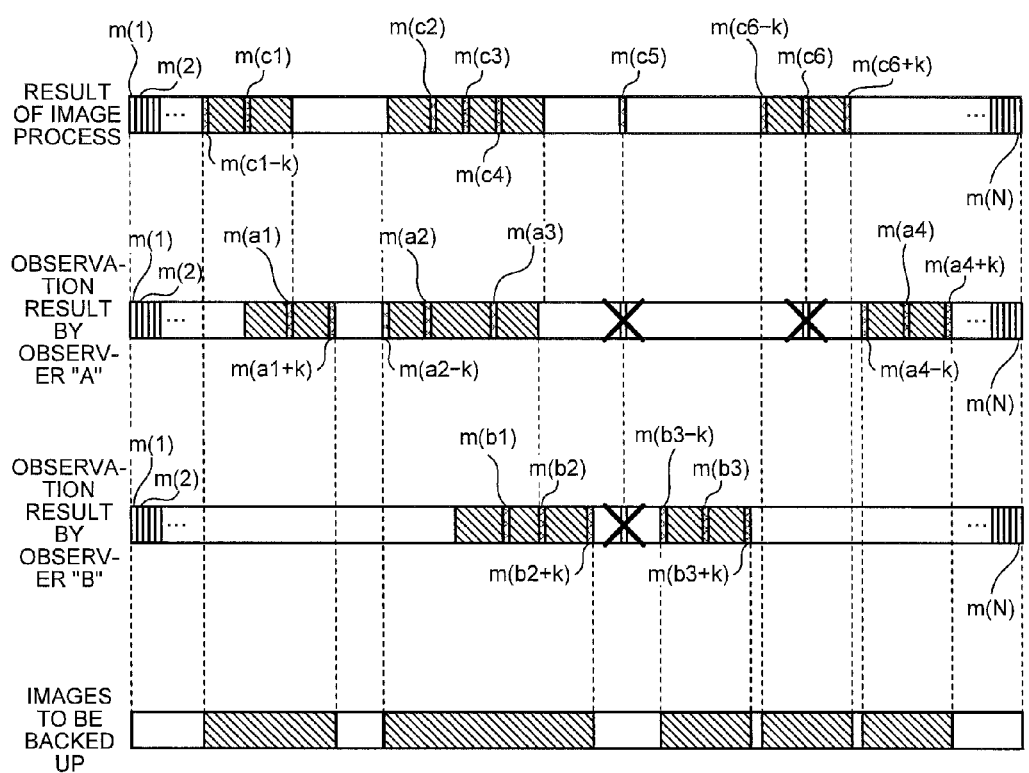
FIG. 14 is a schematic diagram illustrating the process of generating a moving image according to the fifth embodiment of the present invention.

FIG. 14 is a schematic diagram illustrating a process (step S111) of generating a moving image according to the fifth embodiment of the present invention. In the present fifth embodiment, a moving image for backup is generated based on the result of the image process in addition to the observation results to the series of images by the plurality of users (the observers "A" and "B" in FIG. 14). Specifically, in step S122 in FIG. 7, the pieces of identification information of the images $m(c1)$, $m(c2)$, $m(c3)$, $m(c4)$, $m(c5)$, and $m(c6)$ to which a flag is added based on the result of the image process are extracted in addition to the pieces of identification information of the images $m(a1)$, $m(a2)$, $m(a3)$, $m(b1)$, $m(b2)$, $m(b3)$, and $m(a4)$ captured by the observers "A" and "B". Here, $1 \leq c1 < c2 < c3 < c4 < c5 < c6 \leq N$. Then, in next steps S123 to S128, the process is performed based on these pieces of identification information.

However, the image having a flag added thereto based on the result of the image process but deleted from the captured image display area D17 by all users upon the image observation (see step S303) may not be used for the creation of a moving image. For example, in FIG. 14, since the image $m(c5)$ is deleted by both the observers "A" and "B", the image is not used for generating a moving image. On the other hand, the image $m(c6)$ is deleted by the observer "A" but not deleted by the observer "B". Therefore, this image is used for generating a moving image. As a result, the images $m(c1-k)$ to $m(a1+k)$, $m(a2-k)$ to $m(b2+k)$, $m(b3-k)$ to $m(b3+k)$, $m(c6-k)$ to $m(c6+k)$, and $m(a4-k)$ to $m(a4+k)$ are extracted as images to be backed up, and moving images, each including each image group, are generated.

As described above, according to the present fifth embodiment, a moving image as a backup is generated by utilizing the result of the image process, in addition to the observation result by a plurality of users to a series of images. Therefore, backups for images useful for diagnosis can be created without any omission.

Sixth Embodiment

Next, a sixth embodiment of the present invention will be described.

Figure 15:
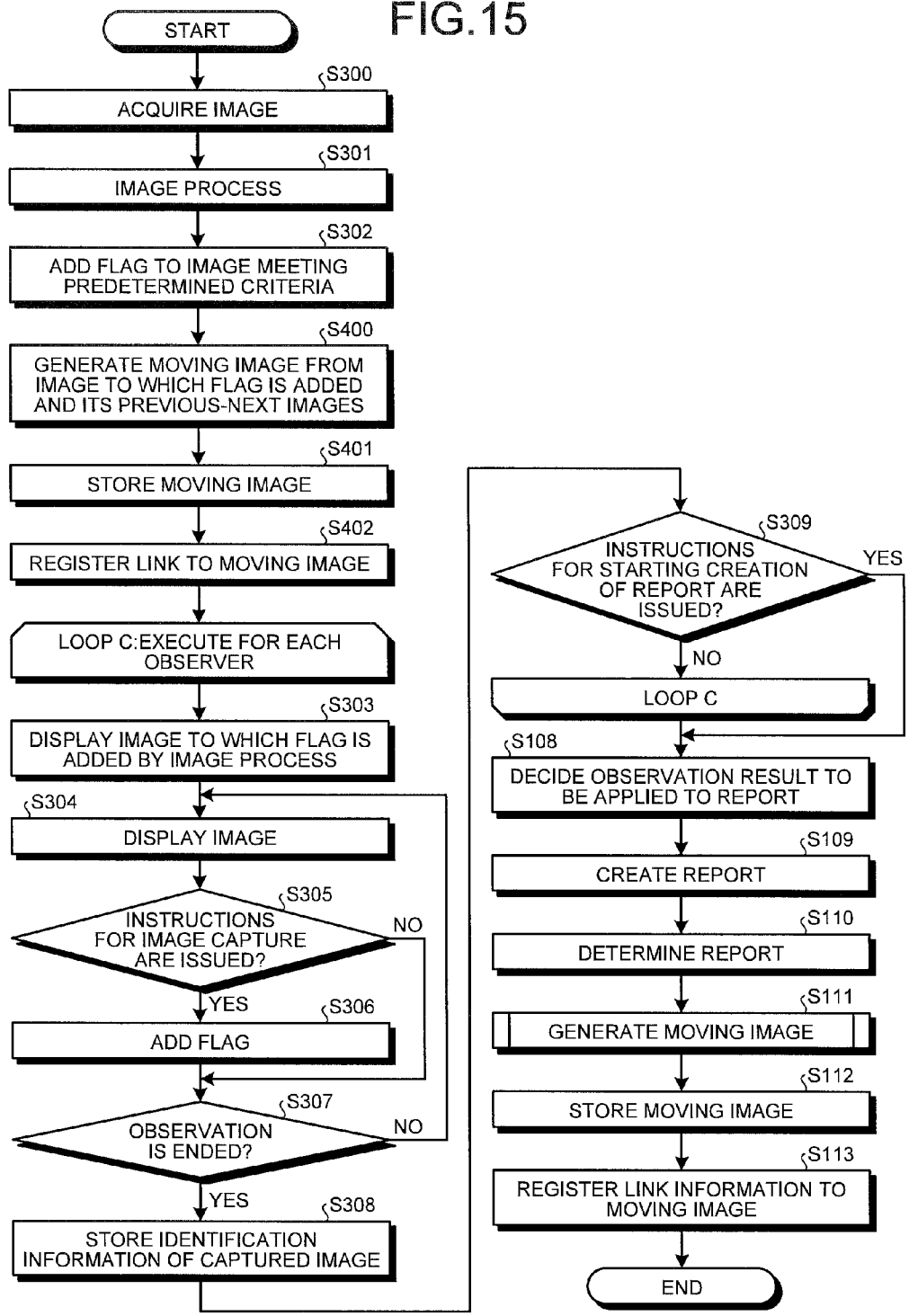
FIG. 15 is a flowchart illustrating an operation of an image management apparatus according to a sixth embodiment of the present invention.

FIG. 15 is a flowchart illustrating an operation of an image management apparatus according to the sixth embodiment of the present invention. Notably, the configuration of the image management apparatus according to the sixth embodiment is similar to that in the first embodiment (see FIG. 2). Steps S300 to S302 in FIG. 15 are similar to those in the fifth embodiment (see FIG. 13).

In step S400 subsequent to step S302, the control unit 16 generates a moving image from the image, to which the flag is added in step S302, and its previous-next images. The process of generating a moving image is performed according to steps S121 to S128 by replacing the captured image illustrated in FIG. 7 as the image to which the flag is added. For example, when a flag is added to the images $m(c1)$, $m(c2)$, $m(c3)$, $m(c4)$, $m(c5)$, and $m(c6)$, image groups of $m(c1-k)$ to $m(c1+k)$, $m(c2-k)$ to $m(c4+k)$, $m(c5-k)$ to $m(c5+k)$, and $m(c6-k)$ to $m(c6+k)$ are extracted as images to be backed up, and a moving image including each of these image groups is generated, as illustrated in FIG. 14.

In next step S401, the control unit 16 stores the moving images generated in step S400 into the backup image storage unit 17.

In next step S402, the control unit 16 registers link information stored in step S401 to the database relating to the examination stored in the examination database storage unit 132.

The operations in steps S303 to S113 are similar to those in the fifth embodiment and the first embodiment. As a result, in FIG. 14, the images $m(c1-k)$ to $m(a1+k)$, $m(a2-k)$ to $m(b2+k)$, $m(b3-k)$ to $m(b3+k)$, $m(c6-k)$ to $m(c6+k)$, and $m(a4-k)$ to $m(a4+k)$ are extracted as images to be backed up, and moving images, each including each image group, are generated (step S111). These moving images are stored in the backup image storage unit 17. Notably, in step S112, the moving images generated in step S111 are stored in a storage area different from that in step S401.

According to the sixth embodiment as described above, a moving image is quickly generated and stored based on the result of the image process, whereby the backup in case of a loss of image data stored in the image storage unit 131 can be ensured until all users finish observation for the series of images.

Second Modification

Next, a second modification of the sixth embodiment of the present invention will be described.

With respect to the above sixth embodiment, the moving image (see step S111) generated based on the observation results by the plurality of users may be written over the moving image (see step S400) generated based on the result of the image process, and stored, in step S112 in FIG. 15. This can reduce the storage capacity for the backups finally stored, while ensuring the backups in case of a loss of image data stored in the image storage unit 131 until all users finish observation for the series of images.

Seventh Embodiment

Next, a seventh embodiment of the present invention will be described.

Figure 16:
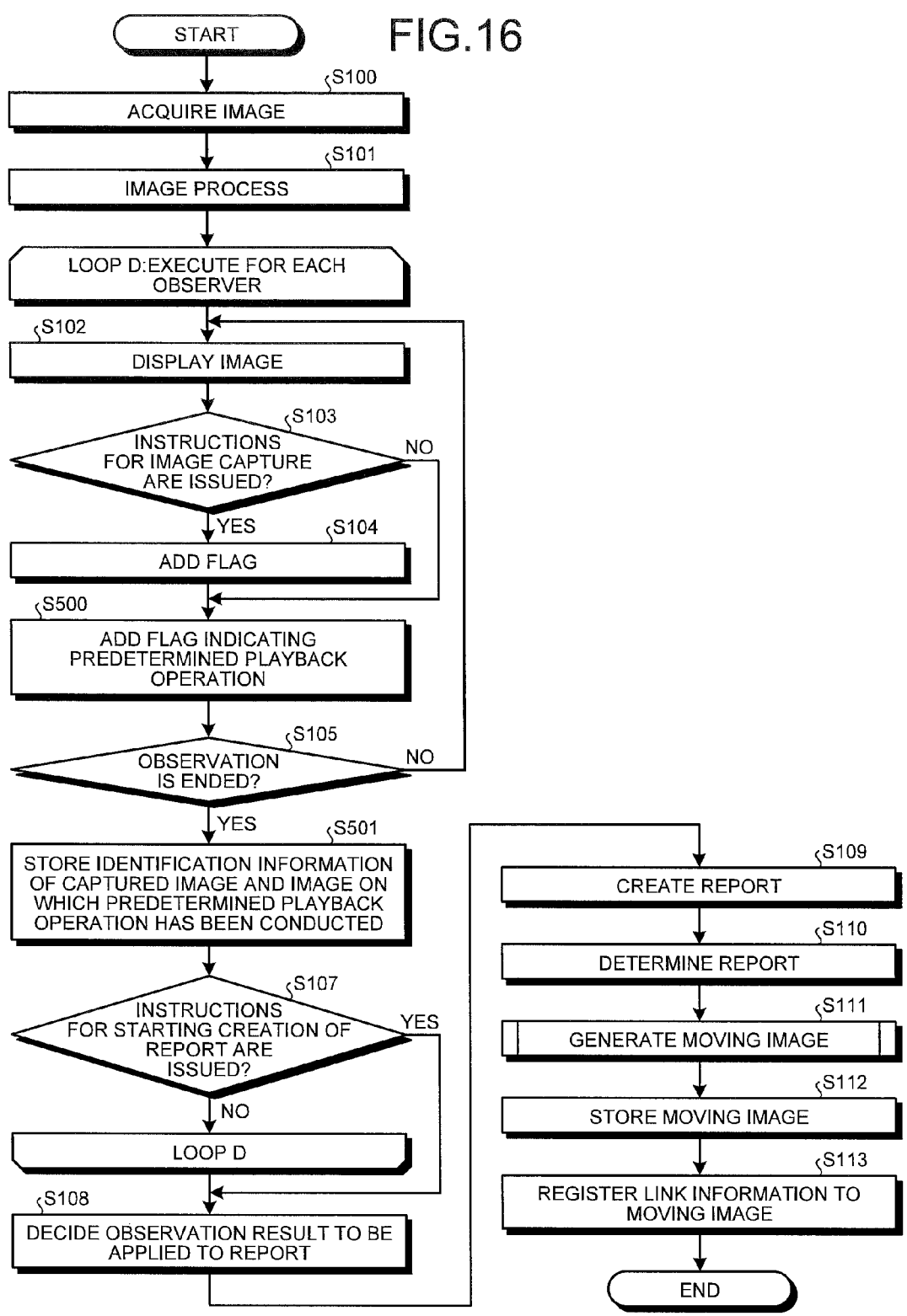
FIG. 16 is a flowchart illustrating an operation of an image management apparatus according to a seventh embodiment of the present invention.

FIG. 16 is a flowchart illustrating an operation of an image management apparatus according to the seventh embodiment of the present invention. Notably, the configuration of the image management apparatus according to the seventh embodiment is similar to that in the first embodiment (see FIG. 2). Steps S100 and S101 in FIG. 16 are similar to those in the first embodiment (see FIG. 4).

Subsequent to step S101, the image management apparatus 1 executes a process of a loop D for each user (observer) observing a series of images. Specifically, in step S102, the display controller 161 sequentially displays a series of images based on the image data on which the image process is performed by the image processing unit 14 on the display unit 15 (see FIG. 3). While images are displayed on the display unit 15, the user can perform a desired playback operation by a predetermined pointer operation on the playback operation button group D14 displayed on the screen D1 using the input unit 11 (e.g., by clicking a desired operation button).

In next step S103, the control unit 16 determines whether a signal for instructing to capture the image currently displayed in the main display area D13 is inputted or not. When the signal for instructing to capture is inputted (step S103: Yes), the control unit 16 adds a flag by which this image is identified as a captured image to this image (step S104), and displays this image in the captured image display area D17 as compressed. On the other hand, when the signal for instructing to capture an image is not inputted (step S103: No), the operation of the image management apparatus 1 proceeds to step S500.

When a predetermined playback operation is conducted on the image currently displayed on the main display area D13, the control unit 16 adds a flag, indicating the playback operation, to the image in step S500. Examples of the predetermined playback operation include a pause, reverse play, repeat, playback with reduced frame rate, and frame advance.

In step S105, the control unit 16 determines whether the observation of the image by the user is ended or not. This determination method is similar to that in the first embodiment (see FIG. 4). When the control unit 16 does not end the observation (step S105: No), the operation of the image management apparatus 1 returns to step S102. On the other hand, when ending the observation (step S105: Yes), the control unit 16 stores into the operation information storage unit 133 for each user, the identification information of the image (captured image) to which the flag is added in step S104 and the identification information of the image to which the flag is added in step S500, i.e., the image on which the predetermined playback operation has been conducted (step S501).

In next step S107, the control unit 16 determines whether a signal for instructing to start the creation of a report is inputted or not. This determination method is similar to that in the first embodiment (see FIG. 4). When the signal for instructing to start the creation of the report is not inputted (step S107: No), the image management apparatus 1 executes the process of the loop D to another user.

On the other hand, when the signal for instructing to start the creation of the report is inputted (step S107: Yes), the operation of the image management apparatus 1 proceeds to step S108. The operations in the following steps S108 to S113 are similar to those in the first embodiment.

Figure 17:
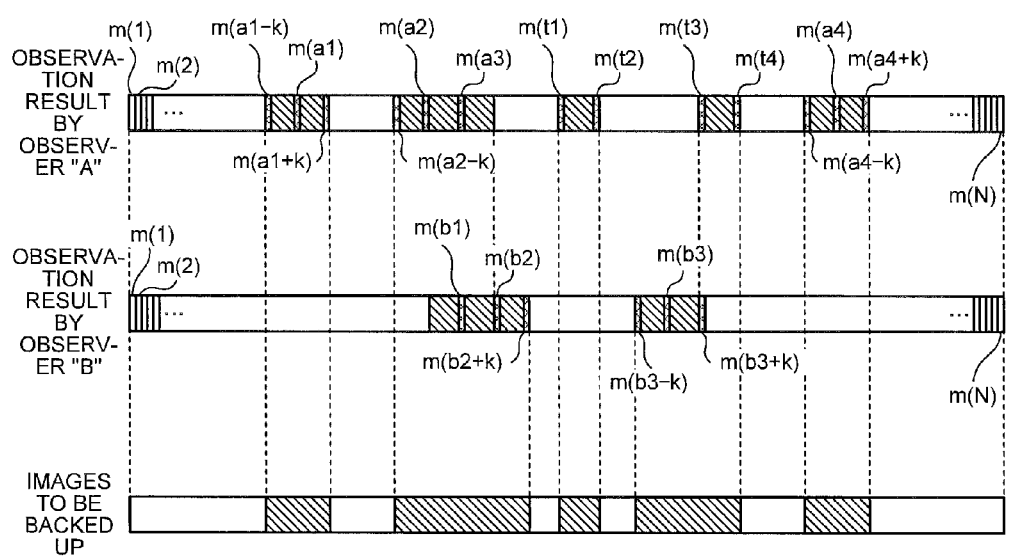
FIG. 17 is a schematic diagram illustrating a process of generating a moving image according to the seventh embodiment of the present invention.

FIG. 17 is a schematic diagram illustrating a process (step S111) of generating a moving image according to the seventh embodiment of the present invention. In the present seventh embodiment, a moving image is generated based on the image receiving a predetermined playback operation in addition to the image captured during the observation of the series of images by each user (in FIG. 17, the observers "A" and "B"). Specifically, in step S122 in FIG. 7, the pieces of identification information of the images m(t1) to m(t2) and m(t3) to m(t4), on which the predetermined playback operation by the observer "A" has been conducted, are acquired in addition to the pieces of identification information of the images m(a1), m(a2), m(a3), m(b1), m(b2), m(b3), and m(a4) captured by the observers "A" and "B". Here, $1 \le t1 < t2 < t3 < t4 \le N$.

Then, in next steps S123 to S128, the process is performed based on these pieces of identification information. The number of the previous-next images of the image on which the predetermined playback operation has been conducted may be the same as or different from the number of the previous-next images of the captured image. In FIG. 17, the numbers of the previous images and the next images of the images m(t1) to m(t2) and m(t3) to m(t4) are zero. As a result, the images m(a1−k) to m(a1+k), m(a2−k) to m(b2+k), m(t1) to m(t2), m(b3−k) to m(t4), and m(a4−k) to m(a4+k) are extracted as images to be backed up, and moving images, each including each image group, are generated.

As described above, according to the present seventh embodiment, images which are considered to be carefully observed by a user, such as an image repeatedly played back, an image played with reduced frame rate, or an image played with frame advance, can be stored as backups.

Third Modification

Next, a third modification of the first to seventh embodiments of the present invention will be described.

In the above first to seventh embodiments, the capsule endoscope 2 including one imaging element and capable of capturing one end of the casing is used, thereby acquiring a series of images in time series in one examination. However, a capsule endoscope including two imaging elements and capable of capturing both ends (e.g., front side and back side) of the casing may be used. In this case, two sets of image groups captured by each of two imaging elements are acquired in one examination, and two sets of moving images can be generated as backups based on the observation results by a plurality of users to each of the two sets of image groups.

Fourth Modification

Next, a fourth modification of the first to seventh embodiments of the present invention will be described.

In the above first to seventh embodiments, more than one moving images (for example, moving images M1 to M4 in FIG. 8) generated as backups are stored as unchanged. However, these moving images may be combined in time series to form one moving image, and this moving image may be stored.

Fifth Modification

Next, a fifth modification of the first to seventh embodiments of the present invention will be described.

In the above first to seventh embodiments, a series of images acquired through an examination is stored in the image storage unit 131, and a moving image for a backup generated from the series of images is stored in the backup image storage unit 17. However, after the moving image for backup is generated, the original series of images may be deleted from the image storage unit 131 according to the user's selection.

According to some embodiments, an image group is extracted from a series of images based on an image associated with information relating to a predetermined operation performed by a plurality of users, whereby images useful for diagnosis can be extracted without any omission, and backups can be created with less storage capacity than in the related art.

The present invention described above is not limited to the first to seventh embodiments and first to fifth modifications, and various modifications are possible according to a specification, and the like. For example, some components may be excluded from all components described in the first to seventh embodiments and first to fifth modifications. It is obvious from the above description that various other embodiments are possible without departing from the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image management apparatus for managing a series of images acquired through an examination, the image management apparatus comprising:
a first image storage unit configured to store, for each examination, the series of images and pieces of identification information of the series of images;
a display unit configured to display the series of images;
an input unit configured to input an operation on an image displayed on the display unit;
an operation information storage unit configured to store first operation information indicating the operation, input by a first user, performed on the series of images that are acquired in one examination and displayed on the display unit, such that the first operation information and identification information of the image on which the operation is performed are associated with one another, and to store second operation information indicating the operation, input by a second user different from the first user, performed on the series of images that are acquired in the one examination and displayed on the display unit, such that the second operation information and identification information of the image on which the operation is performed are associated with one another;
an image extraction unit configured to determine whether or not the identification information of the image associated with the first operation information overlaps with the identification information of the image associated with the second operation information, and to extract an image group from the series of images based on a result of determination; and
a second image storage unit configured to store the image group extracted by the image extraction unit.

2. The image management apparatus according to claim 1, wherein the image extraction unit is configured to extract, as one image group, a plurality of images including at least one image associated with at least one of the first operation information and the second operation information, based on the result of determination.

3. The image management apparatus according to claim 2, wherein the image extraction unit is configured to combine two or more image groups including the image whose identification information is determined to overlap, into one image group, out of a plurality of image groups, each being extracted based on the plurality of images associated with at least one of the first operation information and the second operation information.

4. The image management apparatus according to claim 2, wherein the image extraction unit is configured to extract an image group having images whose pieces of identification information associated with the first operation information and the second operation information are determined to overlap with one another, out of the plurality of images including the at least one image associated with at least one of the first operation information and the second operation information.

5. The image management apparatus according to claim 1, further comprising an image processing unit configured to perform an image process on each image in the series of images, and to add a flag to an image having a predetermined feature based on a result of the image process, wherein
the display unit is configured to display at least one image to which the flag is added by the image processing unit, and
when the first and second users perform an operation of deleting the flag on the at least one image to which the flag is added, the image extraction unit is configured to extract the image group based on: an image other than the image on which the operation of deleting the flag is performed among the at least one image to which the flag is added; the image associated with the first operation information; and the image associated with the second operation information.

6. The image management apparatus according to claim 5, wherein
the image extraction unit is configured to further extract a second image group from the series of images based on the at least one image to which the flag is added, and
the second image storage unit is configured to further store the second image group.

7. The image management apparatus according to claim 5, wherein
the image extraction unit is configured to further extract a second image group from the series of images based on the at least one image to which the flag is added, and
the second image storage unit is configured to store the second image group, and to store the image group by writing over the second image group.

8. The image management apparatus according to claim 1, wherein the image extraction unit is configured to generate a moving image from the extracted image group, and to cause the second image storage unit to store the generated moving image.

9. The image management apparatus according to claim 1, wherein the series of images is a series of in-vivo images acquired by a capsule endoscope that is configured to be introduced into a subject for performing imaging while moving in the subject.

10. The image management apparatus according to claim 1, wherein the operation is at least one of an operation of capturing an image, an operation of adding a label, comment, or annotation to an image, and an operation of selecting an image to be attached to a report.

11. The image management apparatus according to claim 1, wherein the operation is at least one of an operation of bringing an image to a pause to display the image, an operation of repeatedly displaying an image, an operation of displaying an image with reduced frame rate, and an operation of displaying an image with a frame advance.

12. The image management apparatus according to claim 2, wherein the image extraction unit is configured to determine whether or not at least part of pieces of identification information of two or more images associated with at least one of the first operation information and the second operation information, and a predetermined number of images arranged before and after each of the two or more images, overlap with one another, and to extract, as the one image group, the two or more images and the predetermined number of images when the at least part of the pieces of identification information are determined to overlap with one another.

13. The image management apparatus according to claim 2, wherein the image extraction unit is configured to determine whether or not at least part of pieces of identification information of the image associated with at least the first operation information and a predetermined number of images arranged before and after the image, and pieces of identification information of the image associated with at least the second operation information and a predetermined number of images arranged before and after the image, overlap with one another, and to extract the image group having images whose pieces of identification information are determined to overlap with one another.

14. The image management apparatus according to claim 5, wherein the image extraction unit is configured to determine whether or not at least part of pieces of identification information of: at least one of an image other than the image on which the operation of deleting the flag is performed among the at least one image to which the flag is added, the image associated with the first operation information, and the image associated with the second operation information; and a predetermined number of images arranged before and after each of the at least one of the images, overlap with one another.

* * * * *